United States Patent [19]
Goodrich et al.

[11] Patent Number: 6,153,113
[45] Date of Patent: Nov. 28, 2000

[54] METHOD FOR USING LIGANDS IN PARTICLE SEPARATION

[75] Inventors: Raymond P. Goodrich, Denver; Todd Curtis Green, Lakewood, both of Colo.

[73] Assignee: Cobe Laboratories, Inc., Lakewood, Colo.

[21] Appl. No.: 09/253,696

[22] Filed: Feb. 22, 1999

[51] Int. Cl.⁷ .......................... B01D 21/26; G01N 33/537
[52] U.S. Cl. .......................... 210/782; 210/739; 210/786; 210/787; 210/789; 435/2; 436/523; 436/531; 436/532; 494/37
[58] Field of Search .................... 210/782, 787, 210/786, 789, 739; 435/2, 174; 494/37; 436/523, 531, 532

[56] References Cited

U.S. PATENT DOCUMENTS

| | | |
|---|---|---|
| 2,616,619 | 11/1952 | MacLeod . |
| 3,825,175 | 7/1974 | Sartory . |
| 4,035,316 | 7/1977 | Yen et al. . |
| 4,091,989 | 5/1978 | Schlutz . |
| 4,146,172 | 3/1979 | Cullis et al. . |
| 4,187,979 | 2/1980 | Cullis et al. . |
| 4,190,563 | 2/1980 | Bosley et al. . |
| 4,239,729 | 12/1980 | Hasegawa et al. . |
| 4,268,393 | 5/1981 | Persidsky et al. . |
| 4,269,718 | 5/1981 | Persidsky . |

(List continued on next page.)

FOREIGN PATENT DOCUMENTS

| | | |
|---|---|---|
| 057 907 | 8/1982 | European Pat. Off. . |
| 0 214 614 A2 | 3/1987 | European Pat. Off. . |
| 0 323 341 A2 | 7/1989 | European Pat. Off. . |
| 0 406 485 A1 | 1/1991 | European Pat. Off. . |
| 0 408 462 A2 | 1/1991 | European Pat. Off. . |

(List continued on next page.)

OTHER PUBLICATIONS

D.G. Walton et al., Creation of Stable Poly(ethlene oxide) Surfaces on Poly(methl methacrylate) Using Blends of Branched and Linear Polymers; Macromolecules 30:6947–6956 (1997).

Hydrophilic polymer surface prepared with branched additive; C&EN Nov. 17, 1997 p. 30.

Maxim D. Persidsky et al., Separation of Platelet–rich Plasma by Modified Centrifugal Elutriation; Journal of Clinical Apheresis 1:18–24 (1982).

John F. Jemionek et al., Special Techniques for the Separation of Hemopoietic Cells, Current Methodology in Experimental Hematology, 1984, pp. 12–16.

J. Freedman et al., White Cell Depletion of Red Cell and Pooled Random–Donor Platelet Concentrates by Filtration and Residual Lymphocyte Subset Analysis, Transfusion, 1991, vol. 31, No. 5, pp. 433–440.

(List continued on next page.)

*Primary Examiner*—John Kim
*Attorney, Agent, or Firm*—Finnegan, Henderson, Farabow, Garrett & Dunner, L.L.P.

[57] ABSTRACT

A system and method are disclosed for separating particles having different sedimentation velocities. The system includes a container containing a binding substance including first particles and ligands attached to the first particles. When the binding substance is mixed with a liquid carrying at least second and third particles, the ligands bind the first and second particles together to form groups of bound particles. The groups of bound particles are separated from the third particles in a fluid chamber configured to be mounted on a centrifuge rotor. One of the disclosed methods includes forming a saturated fluidized bed of particles to retain the particles groups in the fluid chamber. Another of the disclosed methods includes removing at least some of the first particles after the binding substance is mixed with the liquid carrying second and third particles.

56 Claims, 5 Drawing Sheets

U.S. PATENT DOCUMENTS

| | | |
|---|---|---|
| 4,316,576 | 2/1982 | Cullis et al. . |
| 4,322,298 | 3/1982 | Perisdsky . |
| 4,350,283 | 9/1982 | Leonian . |
| 4,415,665 | 11/1983 | Mosbach et al. ........................ 435/179 |
| 4,416,654 | 11/1983 | Schoendorfer et al. . |
| 4,425,112 | 1/1984 | Ito . |
| 4,464,167 | 8/1984 | Schoendorfer et al. . |
| 4,540,407 | 9/1985 | Dunn . |
| 4,624,923 | 11/1986 | Margel ................................... 435/176 |
| 4,675,117 | 6/1987 | Neumann et al. . |
| 4,680,025 | 7/1987 | Kruger et al. . |
| 4,695,553 | 9/1987 | Wardlaw et al. ........................ 436/177 |
| 4,701,267 | 10/1987 | Watanabe et al. . |
| 4,708,710 | 11/1987 | Dunn, Jr. . |
| 4,708,712 | 11/1987 | Mulzet . |
| 4,710,472 | 12/1987 | Saur et al. ............................... 435/287 |
| 4,752,563 | 6/1988 | Kortright et al. ........................... 435/2 |
| 4,783,336 | 11/1988 | Margel et al. ........................... 424/462 |
| 4,798,579 | 1/1989 | Penhasi . |
| 4,808,151 | 2/1989 | Dunn, Jr. et al. . |
| 4,851,126 | 7/1989 | Schoendorfer . |
| 4,885,137 | 12/1989 | Lork . |
| 4,927,749 | 5/1990 | Dorn ............................................. 435/2 |
| 4,935,147 | 6/1990 | Ullman et al. ........................... 210/695 |
| 4,936,820 | 6/1990 | Dennehey et al. . |
| 4,936,998 | 6/1990 | Nishimura et al. . |
| 4,939,081 | 7/1990 | Figdor et al. . |
| 4,939,087 | 7/1990 | Van Wie et al. . |
| 5,078,671 | 1/1992 | Dennehey et al. . |
| 5,089,146 | 2/1992 | Carmen et al. . |
| 5,100,564 | 3/1992 | Pall et al. . |
| 5,116,724 | 5/1992 | Delaage et al. .............................. 435/2 |
| 5,192,553 | 3/1993 | Boyse et al. ............................ 424/529 |
| 5,198,334 | 3/1993 | Leung ........................................ 435/2 |
| 5,213,970 | 5/1993 | Lopez-Berestein et al. . |
| 5,224,921 | 7/1993 | Dennehey et al. . |
| 5,225,353 | 7/1993 | Berenson et al. ....................... 436/541 |
| 5,229,012 | 7/1993 | Pall et al. . |
| 5,238,812 | 8/1993 | Coulter et al. ........................... 435/7.2 |
| 5,246,829 | 9/1993 | Delaage et al. .............................. 435/2 |
| 5,282,982 | 2/1994 | Wells . |
| 5,298,171 | 3/1994 | Biesel . |
| 5,316,666 | 5/1994 | Brown et al. . |
| 5,316,667 | 5/1994 | Brown et al. . |
| 5,348,739 | 9/1994 | Hellstrand et al. ..................... 424/85.2 |
| 5,360,542 | 11/1994 | Williamson, IV et al. . |
| 5,362,291 | 11/1994 | Williamson, IV . |
| 5,370,802 | 12/1994 | Brown . |
| 5,397,479 | 3/1995 | Kass et al. . |
| 5,409,813 | 4/1995 | Schwartz . |
| 5,429,802 | 7/1995 | Hagiwara et al. . |
| 5,432,054 | 7/1995 | Saunders et al. ........................... 435/2 |
| 5,474,687 | 12/1995 | Van Vlasselaer . |
| 5,501,795 | 3/1996 | Pall et al. . |
| 5,512,453 | 4/1996 | Stevenson ................................ 435/29 |
| 5,529,691 | 6/1996 | Brown . |
| 5,541,107 | 7/1996 | Naughton et al. ............... 435/240.243 |
| 5,547,591 | 8/1996 | Hagihara et al. . |
| 5,549,834 | 8/1996 | Brown . |
| 5,576,185 | 11/1996 | Coulter et al. ......................... 435/7.23 |
| 5,580,465 | 12/1996 | Pall et al. . |
| 5,580,781 | 12/1996 | Naughton et al. ............... 435/240.243 |
| 5,587,070 | 12/1996 | Pall et al. . |
| 5,607,830 | 3/1997 | Biesel et al. . |
| 5,614,106 | 3/1997 | Payrat et al. . |
| 5,622,819 | 4/1997 | Herman . |
| 5,627,029 | 5/1997 | Houseal et al. ............................. 435/6 |
| 5,629,147 | 5/1997 | Asgari et al. ............................... 435/5 |
| 5,635,387 | 6/1997 | Fei et al. ................................. 435/378 |
| 5,639,376 | 6/1997 | Lee et al. ................................ 210/645 |
| 5,641,414 | 6/1997 | Brown . |
| 5,641,622 | 6/1997 | Lake et al. . |
| 5,643,741 | 7/1997 | Tsukamoto et al. ................... 435/7.24 |
| 5,643,786 | 7/1997 | Cohen et al. . |
| 5,656,163 | 8/1997 | Brown ................................. 210/360.1 |
| 5,663,051 | 9/1997 | Vlasselaer .............................. 435/7.23 |
| 5,665,557 | 9/1997 | Murray et al. ......................... 435/7.24 |
| 5,672,346 | 9/1997 | Srour et al. ............................. 424/93.7 |
| 5,674,173 | 10/1997 | Hlavinka et al. . |
| 5,677,136 | 10/1997 | Simmons et al. ...................... 435/7.24 |
| 5,677,139 | 10/1997 | Johnson et al. ........................... 435/29 |
| 5,681,559 | 10/1997 | DiGiusto et al. ...................... 424/93.1 |
| 5,702,823 | 12/1997 | Forrestal et al. ........................ 458/450 |
| 5,722,926 | 3/1998 | Hlavinka et al. . |
| 5,728,378 | 3/1998 | Hellstrand et al. .................... 424/85.7 |
| 5,906,570 | 5/1999 | Langley et al. ........................... 494/45 |
| 5,913,768 | 6/1999 | Langley et al. ............................. 494/7 |
| 5,939,319 | 8/1999 | Hlavinka et al. ....................... 435/325 |

FOREIGN PATENT DOCUMENTS

| | | |
|---|---|---|
| 0 419 346 A2 | 3/1991 | European Pat. Off. . |
| 2658926 | 6/1978 | Germany . |
| 37 00 122 | 7/1988 | Germany . |
| WO 92/21387 | 12/1992 | WIPO . |
| WO 94/02157 | 2/1994 | WIPO . |
| WO 94/25086 | 11/1994 | WIPO . |
| WO 94/27698 | 12/1994 | WIPO . |
| WO 96/33023 | 10/1996 | WIPO . |
| WO 96/40402 | 12/1996 | WIPO . |
| WO 97/30748 | 8/1997 | WIPO . |
| WO 97/43045 | 11/1997 | WIPO . |

OTHER PUBLICATIONS

Nancy M. Heddle et al., The Role of the Plasma from Platelet Concentrates in Transfusion Reactions, The New England Journal of Medicine, vol. 331, No. 10, Sep. 8, 1994, pp. 625–628, 670 and 671.

A. Bruil et al., Asymmetric Membrane Filters for the Removal of Leukocytes From Blood, Journal of Biomed. Materials Research, vol. 25, 1459–1480, 1991.

Sunny Dzik, Leukodepletion Blood Filters: Filter Design and Mechanisms of Leukocyte Removal, Transfusion Medicine Reviews, vol. VII, No. 2, Apr. 1993, pp. 65–77.

Bernard J. Van Wie et al., The Effect of Hematocrit and Recycle on Cell Separations, Plasma Ther. Transfus. Technol. 1986; 7:373–388.

P.D. Drumheller et al., The Effects of RPM and Recycle on Separation Efficiency in a Clinical Blood Cell Centrifuge, Journal of Biomechanical Engineering, Nov. 1987, vol. 109, pp. 324–329.

R.J. Oxford et al., Monitoring and Automated Optimization of a Cell Centrifuge, IEEE/Eighth Annual Conference of the Engineering in Medicine and Biology Society, pp. 925–927. (undated).

R.J. Oxford et al., Interface Dynamics in a Centrifugal Cell Separator, Transfusion, Nov.–Dec., 1988, vol. 28, Nov. 6, pp. 588–592.

A. Tulp et al., A Separation Chamber to Sort Cells and Cell Organelles by Weak Physical Forces, V.A. Sector–Shaped Chamber and Its Application to the Separation of Peripheral Blood Cells, Journal of Immunological Methods 69 (1984), pp. 281–295.

Robert J. Grabske, Separating Cell Populations by Elutriation, pp. 1–8 (undated).

Carl G. Figdor et al., Theory and Practice of Centrifugal Elutriation (CE) Factors Influencing the Separation of Human Blood Cells, Cell Biophysics 5, 105–118 (1983).

P.E. Lindahl, On Counter Streaming Centrifugation in the Separation of Cells and Cell Fragments (1956), pp. 411–415.

C. Almici et al., Counterflow Centrifugal Elutriation: Present and Future, Bone Marrow Transplantation 1993, 12:105–108.

Richard J. Sanderson, Separation of Different Kinds of Nucleated Cells from Blood by Centrifugal Elutriation, Cell Separation Methods and Selected Applications, vol. 1, pp. 153–168. (undated).

P.C. Keng et al., Characterization of the Separation Properties of the Beckman Elutriator System, Cell Biophysics 3 (1981), pp. 41–56.

Biofil, Systems for Filtration of Haemocomponents. (undated).

Claes, F. Hogman, Leucocyte Depletion of Blood Components, 1994, pp. 1, 156–173.

A.S. Buchanan et al., Principle of a Counter–streaming Centrifuge for the Separation of Particles of Different Sizes, Nature, Apr. 24, 1948, pp. 648–649.

"Cost–Effectiveness of Leukocyte Depletion of Blood Components", Presented at the 1993 AABB Meeting Miami Beach, FL.

I. Sniecinski, Prevention of Immunologic and Infectious Complications of Transfusion by Leukocyte Depletion, Prevention of Complications of Transfusion Chapter 18; pp. 202–211. (undated).

Benefits of Leukocyte Filtration for Red Cell and Platelet Blood Products, Transfusion Associated CMV (1994), pp. 1–18.

G. Stack et al., Cytokine Generation in Stored Platelet Concentrates, Transfusion, 1994; 34:20–25.

N. M. Heddle et al., A prospective study to identify the risk factors associated with acute reactions to platelet and red cell transfusions; Transfusion, 1993; 33:794–797.

H. Brandwein et al., Asahi Sepacell PL10A Leukocyte Removal Filter:Efficiency with Random Donor Platelet Pools, PALL Technical Report. (undated).

J. Whitbread et al., Performance Evaluation of the Sepacell PL10A filter and Pall PXL 8 filter: Measurement of Leukocyte Residuals and Consistency, PALL Technical Report. (undated).

R. Brown et al., Evaluation of a new separation method utilizing plasma recirculation and autoelutriation, Transfusion, 1994; vol. 34, Supp.

Richard J. Sanderson et al., Design Principles for a Counterflow Centrifugation Cell Separation Chamber, Analytical Biochemistry 71, 615–622(1976).

Designed to Provide the Reliability and Performance to Harvest a High Yield Component Product, The Haemonetics V50 Apheresis System. (undated).

Haemonetics Mobile Collection System Owner's Operating and Maintenance Manual, 1991 pp. 3–2 through 3–7 and pp. 1–6.

E.A. Burgstaler et al., White Blood Cell Contamination of Apheresis Platelets Collected on the COBE Spectra, COBE Blood Component Technology. (undated).

T.H. Price et al., Platelet Collection Using the COBE Spectra, COBE Blood Component Technology. (undated).

Nancy Besso et al., Asahi Sepacell PL–10A Leukocyte Removal Filter: Effect of Post–Filtration Flush With Saline, PALL Technical Report. (undated).

Harvey J. Brandwein et al., Asahi Sepacell PL–10A Leukocyte Removal Filter Description and Review of Claims, PALL Technical Report. (undated).

"Lower is Better!", (flyer) PALL Biomedical Products Company. (undated).

Judy H. Angelbeck, Adverse Reactions to Platelet Transfusion, Risks and Probable Causes (1994), pp. 1–14.

Centrifugual Elutriation, Beckman pp. 1–7, vi (undated).

AS 104 Cell Separator, Fresenius. (undated).

CS–3000 Blood Cell Separator, Powerful Technology, Fenwal Laboratories. (undated).

Baxter CS–3000 Plus Blood Cell Separator Operator's Manual (7–19–3–136).

The Mobile Collection System gives you easier access to more donors than ever before, Haemonetics (Sep. 1992).

LRF6/LRF10, High Efficiency Leukocyte Removal Filter Systems For Platelets, PALL Biomedical Products Corporation. (undated).

J. Whitbread et al., Reduction of C3A Fragment Levels Following Leukodepletion Using a PALL PXL8 Filter. (undated).

T. A. Takahashi et al., Bradykinin Formation in a Platelet Concentrate Filtered with a Leukocyte–removal Filter Made of Nonwoven Polyester Fibers with a Negatively Charged Surface. (undated).

Baxter CS–3000 Plus Blood Cell Separator pp. 1–18. (1990).

J.F. Jemionek, Variations in CCE Protocol for Cell Isolation, Elutriation, pp. 17–41. (undated).

Brief Operating Instructions, Fresenius MT AS 104 blood cell separator, 4/6.90(OP).

English language abstract of SU 1725117 A.

English language abstract of SU 1255136.

English language abstract of SU 1236366.

English language abstract of SU 1091071.

English language abstract of DE 3734170.

Multi Chamber Counterflow Centrifugation System, Dijkstra Vereenigde B.V., 13 pgs. (undated).

Baxter CS–3000 Plus Blood Cell Separator, Technology With a Mind You Can Own, 1990.

Aart Plas, Theo de Witte, Hans Wessels, and Clements Haanen, "A New Multi–chamber Counterflow Centrifugation Rotor with High–separation Capacity and Versatile Potentials," Experimental Hematology 16:355–359 (1988) International Society for Experimental Hematology.

Michael G. Kauffman, Stephen J. Noga, Thomas J. Kelly, and Albert D. Donnenberg, "Isolation of Cell Cycle Fractions by Counterflow Centrifugal Elutriation," Analytical Biochemistry 191, 41–46 (1990).

A. Faradji, A. Bohbot, M. Schmitt–Goguel, J.C. Siffert, S. Dumont, M.L. Wiesel, Y. Piemont, A. Eischen, J.P. Bergerat J. Bartholeyns, P. Poindron, J.P. Witz, F. Oberling, "Large Scale Isolation of Human Blood Monocytes by Continuous Flow Centrifugation Leukapherisis and Counterflow Centrifugation Elutriation for Adoptive Cellular Immunotherapy in Cancer Patients," Journal of Immunological Methods 174 (1994) 297–309.

Ino K. Gao, Stephn J. Noga, John E. Wagner, Carol A. Cremo, Janice Davis and Albert D. Donnenberg, "Implementation of a Semiclosed Large Scale Centrifugal Elutriation System," Journal of Clinical Apheresis 3:154–160 (1987).

Owen M. Griffith, "Separation of T and B Cells from Human Peripheral Blood by Centrifugal Elutriation," Analytical Biochemistry 87, 97–107 (1978).

Carl G. Figdor, Willy S. Bont, Ivo Touw, Johan de Roos, Eddy E. Roosnek and Jan E. de Vries, "Isolation of Functionally Different Human Monocytes by Counterflow Centrifugation Elutriation," Blood, vol. 60, No. 1, 46–52, Jul. 1982.

Jan Marc Orenstein, et al., "Microemboli Observed in Deaths Following Cardiopulmonary Bypass Surgery: Silicon Antifoam Agent and Polyvinyl Chloride Tubing as Sources of Emboli," Human Pathology, vol. 13, No. 12, (Dec. 1982), pp. 1082–1090.

I.R. Schmolka, "Polyalkylene Oxide Block Copolymers" Nonionic Surfactants, Chapt. 10, p. 300–371 (1967).

Lee, et al., "Protein–resistant surfaces prepared by PEO–containing block copolymer surfactants," Journal of Biomedical Materials Research, vol. 23, 351–368 (1989).

Mansoor Amiji et al., "Prevention of protein adsorption and platelet adhesion on surfaces by PEO/PPO/PEO triblock copolymers," Biomaterials 1992, vol. 13, No. 10, 682–692.

Hymes, et al., Pluronics: First Use as a Plasma Expander (Abstract) Abstracts of the 40th Scientific Sessions, Supplement to Circulation vols. XXXV and XXXVI, (Oct. 1967).

Yoshimasa Miyauchi, et al., "Adjunctive Use of a Surface–Active Agent in Extracorporeal Circulation," Supplement I to Circulation vols. XXXIII and XXXIV, Apr. 1966 p. 171–177.

E.S. Wright, et al., "Fat globulemia in extracorporeal circulation," Surgery, vol. 53 No. 4, pp. 500–504, (Apr. 1963).

R. Champlin, "Purging: the separation of normal from malignant cells for autologous transplantation," Transfusion 1996, vol. 36, 910–918.

Jan Grimm, et al., "Separation and characterization of mobilized and unmobilized peripheral blood progenitor cells by counterflow centrifugal elutriation", Experimental Hematology 23:535–544 (1995).

Herbein, et al., "Isolation and Identification of Two CD34+ Cell Subpopulations from Normal Human Peripheral Blood," Stem Cells 1994:12:187–197.

L. Teofili, et al., "Separation of chemotherapy plus G–CSF–mobilized peripheral blood mononuclear cells by counterflow centrifugal elutriation: in vitro characterization of two different CD34+ cell populations," Bone Marrow Transplantation (1996) 18, 421–425.

Keng, et al., "Characterization of the biophysical properties of human tumor and bone marrow cells as a preliminary step to the use of centrifugal elutriation in autologous bone marrow transplantation,"Radiation Oncology Biology Physics (Oct. 1984) vol. 10, No. 10, 1913–1922.

Lutz, et al., "Large–scale cell separation by centrigugal elutriation," Analytical Biocemistry 200, 376–380 (1992).

Orlic, et al., "Biological properties of subpopulations of pluripotent Hematopoietic stem cells enriched by elutriation and flow cytometry," Blood Cells (1994) 20: 107–120.

Hillyer, et al., "CD34+ progenitors and colony–forming units–granulocyte macrophage are recruited during large–volume leukapheresis and concentrated by counterflow centrifugal elutriation," Transfusion, vol. 33, No. 4, pp. 316–321 (1993).

Gengozian, et al., "Separation of feline bone marrow cells by counterflow centrifugal elutriation," Transplantation, vol. 60, 836–841, No. 8, Oct. 1995.

Nichol, et al., "Enrichment and Characterization of peripheral blood–derived megakarycocyte progenitors that mature in short–term liquid culture," Stem Cells 1994: 12: 494–505.

Ossevoort, et al., "A rapid isolation procedure for dendritic cells from mouse spleen by centrifugal elutriation," Journal of Immunological Methods 155 (1992) 101–111.

P.C. Keng, "High–Capacity Separation of Homogeneous Cell Subpopulations by Centrifugal Elutriation," Cell Separation Science and Technology, 103–112 (1991).

Pretlow II, et al., "Sedimentation of Cells: An Overview and Discussion of Artifacts," Cell Separation: Methods and Selected Applications, vol. 1, 41–60, (1982).

Wagner, et al., "Lymphocyte Depletion of Donor Bone Marrow by Counterflow Centrifugal Elutriation: Results of a Phase I Clinical Trial," Blood, 72, No. 4, (1988), 1168–1176.

De Witte, et al., "Cell Size Monitored Counterflow Centrifugation of Human Bone Marrow Resulting in Clonogenic Cell Fractions Substantially Depleted of Small Lymphocytes," Journal of Immunological Methods, 65 (1983) 171–182.

Noga, et al., "Using Elutriation to Engineer Bone Marrow Allografts," Bone Marrow Purging and Processing, 345–361, (1990).

Keng, et al., "Evaluation of Cell Subpopulations Isolated from Human Tumor Xenografts by Centrifugal Elutriation," Int. J. Radiation Oncology Biol. Phys. vol. 18, pp. 1061–1067 (1990).

Monroy, et al., "Centrifugal Elutriation," Plasma Ther. Transfus. Technol. 1986, vol. 7: 389–394.

Uchida, et al., "Searching for hematopoietic stem cells II. The heterogeneity of Thy–1.1$^{lo}$Lin$^{-lo}$Sca–1+ mouse hematopoietic cells separated by counterflow centrifugal elutriation," Experimental Hematology 24:649–659 (1996).

Jones, et al., "Separation of pluripotent haematopoietic stem cells from spleen colony forming cells," Nature, vol. 347, 188–189 (Sep. 1990).

Suzuki, et al., "Centrifugal elutriation and characterization of tumor cells from venous blood of tumor–bearing mice: possible relevance to metastasis," Cancer Research 44, 3505–3511, (Aug. 1994).

Schattenberg, et al., "Allogeneic Bone Marrow Transplantation for Leukemia with Marrow Grafts Depleted of Lymphocytes by Counterflow Centrifugal," Blood, vol. 75, No. 6 (Mar. 1990), pp 1356–1363.

Van Es, et al., "An Improved Method for the Fractionation of Human Blood Cells by Centrifugal Elutriation," Analytical Biochemistry 103, 295–301, (1980).

Contreras, et al., "An Improved Technique for the Negative Selection of Large Numbers of Human Lymphocytes and Monocytes by Counterflow Centrifugation–Elutriation," Cellular Immunology 54, 215–229 (1980).

Stevenson, et al., "A System for Obtaining Large Numbers of Cryopreserved Human Monocytes Purified by Leukapheresis and Counter–current Centrifugation Elutriation (CCE)," Journal of Immunological Methods, 62 (1983), 353–355.

Jemionek, et al., "Fractionation of mammalian bone marrow by counterflow centrifugation–elutriation using a continuous albumin gradient:; analysis of granulocyte–macrophage colony–forming units," British Journal of Haematology, 1982, 50, 257–267.

De Witte, et al., "Depletion of donor lymphocytes by counterflow centrifugation successfully prevents acute graft–versus–host disease in matched allogeneic marrow transplantation," Blood vol. 67, No. 5, (May 1986) 1302–1308.

Hemasure to Collaborate with American Red Cross on Tumor Cells Removal Technology, PR Newswire HemaSure Inc. (Jan. 30, 1996).

Kolber, et al., "Target Cell Lysis by Cytototoxic T Lymphocytes Redirected by Antibody–Coated Polystyrene Beads," The Journal of Immunology, vol. 143, 1461–1466, No. 5, Sep. 1989.

Blazar, et al., "Comparison of Three Techniques for the ex vivo Elimination of T Cells from Human Bone Marrow," Experimental Hematology, 13:123–128 (1985).

Quinones, et al., "Extended–Cycle Elutriation to Adjust T–Cell Content in HLA–Disparate Bone Marrow Transplantation," Blood vol. 82, No. 1, 307–317, (1993).

G.B. Nash, "Filterability of Blood Cells: Methods and Clinical Applications" Biorheology, 27: 873–882 (1990).

Linda A. Chambers, "Characteristics and Clinical Application of Blood Filters," Transfus.Sci. 1989; 10: 207–218.

Lennie, et al., "Filterability of White Blood Cell Subpopulations, Separated by an Improved Method," Clinical Hemorheology, vol. 7, pp. 811–816, (1987).

Marcus, et al., "CFU–GM and T cell subsets in young red cell collections," Trans., vol.. 24, No. 5, p. 379–381 (1984).

Bruisten, et al., "Efficiency of white cell filtration and a freeze–thaw procedure for removal of HIV–infected cells from blood," Transfusion vol. 30, p. 833–837 (1990).

Nash, et al., "Methods and theory for analysis of flow of white cell sub–populations through micropore filters," British Journal of Haematology, 1988, 70: 165–170.

Ciuffetti, et al., "Human leucocyte rheology and tissue ischaemia," European Journal of Clinical Investigation (1989) 19, 323–327.

van Prooijen, et al., "Prevention of primary transfusion–associated cytomegalovirus infection in bone marrow transplant recipients by the removal of white cells from blood components with high–affinity filters," British Journal of Haematology (1994) 87, pp. 144–147.

Palathumpat, et al., "Different Subsets of T cells in the adult mouse bone marrow and spleen induce or supress acute graft–versus–host disease," The Journal of Immunology, vol. 149, p. 808–817 No. 3 (Aug. 1992).

Palathumpat, et al., "Studies of CD4– CD8– $\alpha\beta$ Bone Marrow T Cells with Suppressor Activity," Journal of Immunology, vol. 148, p. 373–380 (Jan. 1992).

Schmidt–Wolf, et al., "T–cell subsets and suppressor cells in human bone marrow," Blood, vol. 80 No. 12, (Dec. 1992) pp. 3242–3250.

Palathumpat, et al., "A novel cell separation technique for the enrichment of committed and uncommitted human hematopoietic progenitor cells and T cell depletion," Experimental Hematology Today (1995), p. 1–7.

Strang, et. al., "Density adjusted cell sorting (DACS), a novel cell separation method using high density microspheres in combination with customized density gradient solution to enrich or deplete specific cell sub–populations," Experimental Hematology Today (1995) p. 1–6.

Shpall, et al., "Bone Marrow Metastases," Hemtology/Oncology Clinics of America, vol. 10 No. 2, (Apr. 1996) p. 321–343.

Trickett, et al., "Tumour cell purging for autologous bone marrow transplantation," Medical Laboratory Sciences, vol. 47, (1990) p. 120–131.

Gribben, et al., "Immunologic purging of marrow assessed by PCR before autologous bone marrow transplantation for B–cell lymphoma," The New England Journal of Medicine, vol. 325, No. 22, 1525–1532 (1991).

Jansen, et al., "Immunomagnetic CD4+ and CD8+ cell depletion for patients at high risk for severe acute GVHD," Bone Marrow Transplantation (1996) vol. 17, p. 377–382.

Quinones, et al., "Inhibition of Cytotoxic T cell lysis by anti–CD8 monoclonal antibodies: studies with CD3–targeted cytolysis of nominal antigen–negative targets," The Journal of Immunology vol. 142, p. 2200–2206. (1989).

Lucas, et al., "Alternative donor sources in HLA–mismatched marrow transplantation: T cell depletion of surgically cadaveric marrow," Marrow Transplanation (1988) 3, 211–220.

Lundsted, et al., "The synthesis and Properties of block copolymer polyol surfactants," p. 1–111. (undated).

Plurafac RA–20 Linear Alcohol Alkoxylate, Plurafac RA–30 Linear Alcohol Alkoxylate, Technical Bulletin, BASF Corp. 1987, p. 1–29.

"Diagnostic and Therapeutic Technology Assessment (DATTA) Autologous Bone Marrow Transplantation," Jul. (1986) vol. 256, No. 1.

Richard G. Miller, et al., "Separation of Cells by Velocity Sedimentation", J. Cell. Physiol., vol. 73, pp. 191–202. (1969).

Pluronic & Tetronic Surfactants, Technical Bulletin, BASF Corp. 1989, p. 1–28.

Palathumpat, et al., "Treatment of $BCL_1$ leukemia by transplantation of low density fractions of allogeneic bone marrow and spleen cells[1]", The Journal of Immunology, vol. 148, pp. 3319–3326, No. 10, (May 1992).

Bernard John Van Wie, Conceptualization and Evaluation of Techniques for Centrifugal Separation of Blood Cells: Optimum Process Conditions, Recycle and Stagewise Processing, Dissertation, 1982, pp. 27–58.

Briddell, et al., Purification of CD34+ Cells Is Essential for Optimal Ex Vivo Expansion of Umbilical Cord Blood Cells: Journal of Hematotherapy vol. 6, pp. 145–150, 1997.

Deenning–Kenda al., Optimal processing of human umbilical cord blood for clinical banking: Experimental Hematology vol. 24, pp. 1394–1401, 1996.

Tech. Note #13c, Covalent Coupling Protocols, Bangs Laboratories, Inc., Microsphere Specialists, pp. 1–9. (undated).

Microsphere Selection Guide, Bangs Laboratories, pp. 1–16, Mar. 1997.

Toyopearl Column Packing Manual, pp. 1–12, Supelco, Inc. 1996.

Information About BLI–(Apr. 18, 1997), Bangs Laboratories, Inc. pp. 1–3. (1997).

Dynal Product Catalogue 1996, HLA Microbiology, Molecular Biology Cellular Immunology.

Axen, Rolf et al., Chemical Coupling of Peptides and Proteins to Polysaccharides by Means of Cyanogen Halides, Nature, vol. 214, Jun. 24, 1967, pp. 1302–1304.

Yoshioka, Masanori, et al., Immobilization of ultra–thin layer of monoclonal antibody on glass surface, Journal of Chromatography; 566 (1991) 361–368, Biomedical Applications, Elsevier Science Publishers B.V., Amsterdam.

BioDesign Inc. of New York, BioDesign CellMicroSieves™, 2 pages, May 1998.

Miltenyi Biotec, MACS the Easiest, Fastest and Most Reliable. (undated).

ISOLEX™ 300 Magnetic Cell Separator Yielding the Purity, Biotech Group, Baxter (6 pages). (undated).

CEPRATE®SC, Stem Cell Concentration System, Continuous Flow Technology, CellPro, Inc. (undated).

Hirn–Scavennec, Joell, et al., Elimination of Leukemia Cells from Human Bone Marrow Using Floating Beads[1], Transplantation, vol. 46, 558–563, No. 4, Oct. 1988.

METHOD FOR USING LIGANDS IN PARTICLE SEPARATION

This application is related to U.S. Pat. No. 5,674,173, issued on Oct. 7, 1997; U.S. patent application Ser. No. 08/423,583, filed on Apr. 18, 1995 (abandoned); U.S. patent application Ser. No. 08/634,167, filed on Apr. 18, 1996, U.S. Pat. No. 5,939,319; and U.S. patent application Ser. No. 09/009,378, filed on Jan. 20, 1998 (pending). The entire disclosure of this U.S. patent and the entire disclosures of these U.S. patent applications are incorporated herein by reference.

BACKGROUND OF THE INVENTION

1. Field of the Invention

The present invention relates to a system and method for separating particles. The invention has particular advantages in connection with separating blood components, such as antigen-specific blood cells.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of processes where particles are either separated from one another or from liquid.

In the medical field, it is often necessary to filter blood. Whole blood consists of various liquid components and particle components. Sometimes, the particle components are referred to as "formed elements." The liquid portion of blood is largely made up of plasma, and the particle components primarily include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle constituents are related according to size, in order of decreasing size, as follows: white blood cells, red blood cells, and platelets.

Although blood is primarily made up of white blood cells, red blood cells, and platelets, there are a number of other particle components of blood. For example, blood includes T-cells (a type of white blood cell), B-cells, monocytes (another type of white blood cell), stem cells, and NK cells. Most of these particles have similar sizes and/or densities. However, some of these particles have different surface chemistry characteristics designated with a specific "CD+" marker or symbol. For example, T-cells include CD2+ cells, CD3+ cells, CD4+ cells, and CD8+ cells; B-cells include CD9+ cells, CD10+ cells, and CD19+ cells; monocytes include CD14+ cells; stem cells include CD34+ cells; leukocytes include CD45+ cells; and NK cells include CD56+ cells. Corresponding antibodies, identified with an "anti-CD" marker or symbol, are capable of binding to these cells having particular surface chemistry characteristics. For example, anti-CD2 is capable of binding with CD+2 cells; anti-CD3 is capable of binding with CD3+ cells; and anti-CD4 is capable of binding with CD+4 cells. In a similar manner, anti-CD8, anti-CD9, anti-CD10, anti-CD14, anti-CD15, anti-CD19, anti-CD20, anti-CD34, anti-CD38, anti-CMRF-44, anti-CD45, anti-CD56, anti-CD83, anti-glyocophorin, anti-cytokeratin, and anti-EPCAM are capable of binding with CD8+ cells, CD9+ cells, CD10+ cells, CD14+ cells, CD15+ cells, CD19+ cells, CD20+ cells, CD34+ cells, CD38+ cells, CMRF44+ cells, CD45+ cells, CD56+ cells, CD83+ cells, glyocophorin+ cells, cytoketatin+ cells, and EPCAM+ cells, respectively, for example.

Most current separation devices rely on density and size differences or surface chemistry characteristics to separate and/or filter blood components for transfusion or reinfusion purposes. Typically, blood components are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Although some centrifugal separation techniques are effective at separating some blood components from one another, many centrifugal separation processes are not capable of producing a highly purified end product.

In one type of separation procedure, a peripheral blood collection (withdrawn from an artery or vein) or a bone marrow blood collection is purified in a centrifugal separation process to isolate what is known as a peripheral blood cell collection or bone marrow blood cell collection, respectively. The peripheral blood cell collection or bone marrow blood cell collection primarily includes plasma, red blood cells, white blood cells (leukocytes, such as T-cells and monocytes), and stem cells. These cell collections also may include amounts of B-cells and NK cells.

After undergoing a therapeutic treatment, such as chemotherapy or radiation therapy, to eliminate cancerous tumor cells, cancer patients often receive a transfusion of a peripheral blood cell collection or a bone marrow blood cell collection to replace stem cells destroyed as a side effect of the treatment. To reduce risks associated with infusing blood components from a foreign donor, some of these transfusions are autologous, where blood components collected from the patient are later reinfused back to the patient. Another type of transfusion, known as allogenic transfusion, involves collecting blood components from a donor and then infusing the collected blood components into a recipient who is different from the donor. Sometimes, however, the recipient of an allogenic transfusion experiences a disease commonly known as graft versus host disease. In graft versus host disease, particular T-cells, which may accompany the blood components, are infused into the recipient and "recognize" that the recipient's body is "foreign" from that of the donor's. These T-cells "attack" healthy cells in the recipient's body, rather than performing a normal immunological protective function. Recent studies have shown that a particular type of T-cells, namely CD8+ cells, could cause graft versus host disease.

Several prior attempts to separate stem cells from T-cells prior to reinfusion have been made. In one separation method, a selective antibody, anti-CD34, is introduced into a collected blood component sample after separating a substantial number of platelets and red blood cells from the sample. This selective antibody chemically attaches to stem cells (CD34+ cells) to "mark" them. To separate the marked stem cells from the remaining blood components, the collected blood components are passed between stationary beads coated with a material which chemically bonds with the selective antibody. These chemical bonds retain the marked stem cells on the beads to filter them from the remaining blood components.

To remove the marked stem cells from the beads, an operator agitates the beads or flushes a chemical solution through the beads to break the chemical bonds between the material and selective antibody. This separation process, however, is extremely expensive, tedious, and time consuming and often requires an initial centrifugation procedure to remove platelets and red blood cells. In addition, sometimes the beads do not remove a significant number of stem cells, and a substantial number of T-cells often remain in the separated end product.

In another type of separation procedure, magnetic particles or fluid having an attached antibody, anti-CD34, are added to a blood component collection. The antibody binds with stem cells (CD34+ cells) in the sample to link the magnetic particles and stem cells together. To separate the stem cells, a magnetic separator is used to attract the magnetic substance and stem cells, and linked a substance is then added to break the chemical bonds between the stem cells and magnetic substance.

Although this separation procedure is capable of separating some stem cells and T-cells, it is expensive and labor intensive. A significant number of T-cells remain in the separated end product and a sizable number of stem cells are not recovered. In addition, the substances added to the blood sample in both the bead separation process and the magnetic separation process are potentially toxic if they are infused along with the separated blood components.

Centrifugal elutriation is another process used to separate T-cells from stem cells. Normally, this process is used to separate cells suspended in a liquid medium without the use of chemical antibodies. In one common form of elutriation, a cell batch is introduced into a flow of liquid elutriation buffer. This liquid which carries the cell batch in suspension, is then introduced into a funnel-shaped chamber located on a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal elutriation separates particles having different sedimentation velocities. Stoke's law describes sedimentation velocity (SV) of a spherical particle, as follows:

$$SV = \frac{2}{9} \frac{r^2(\rho_p - \rho_m)g}{\eta}$$

where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in the Stoke's equation and the density of the particle is not, the size of a cell, rather than its density, greatly influences its sedimentation rate. This explains why larger particles generally remain in a chamber during centrifugal elutriation, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

Further, a Coriolis jetting effect takes place when liquid and particles flow into an elutriation chamber from a high centrifugal field toward a lower centrifugal field. The liquid and particles turbulently collide with an inner wall of the chamber facing the rotational direction of the centrifuge. This phenomenon mixes particles within the chamber and reduces the effectiveness of the separation process. Coriolis jetting also shunts flow of liquid and particles along the inner wall of the elutriation chamber from the inlet directly to the outlet. Thus, particles pass around the elutriative field to contaminate the end product.

If the combined density of particles and liquid in the elutriation chamber is significantly greater than the density of liquid entering the chamber, Coriolis jetting increases. This is because the relatively low density liquid entering the elutriation chamber encounters increased buoyant forces tending to accelerate the flow of liquid toward the outlet of the elutriation chamber. When the accelerated flow of liquid encounters tangential forces in the chamber, the flow of liquid may form a Coriolis jet capable of carrying larger, relatively faster sedimenting particles around the elutriative field and through an outlet of the chamber.

Particle mixing by particle density inversion is an additional problem encountered in some prior elutriation processes. Fluid flowing within the elutriation chamber has a decreasing velocity as it flows in the centripetal direction from an entrance port toward an increased cross-sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

For these and other reasons, there is a need to improve particle separation.

SUMMARY OF THE INVENTION

Accordingly, the present invention is directed to a system and method that substantially obviate one or more of the limitations of the related art. To achieve these and other advantages and in accordance with the purpose of the invention, as embodied and broadly described herein, the invention includes a system for separating particles. The system includes a fluid chamber and a container containing a binding substance. The fluid chamber has an inlet, an outlet, and a wall. The wall of the fluid chamber has an inner surface defining an interior having a maximum cross-sectional area at a position between the inlet and the outlet. This interior converges from the position of the maximum cross-sectional area toward the inlet and also converges from the position of the maximum cross-sectional area toward the outlet. The binding substance in the container includes first particles and ligands attached to the first particles. At least some of the ligands are capable of binding with second particles to form groups of bound particles capable of being separated from third particles in the fluid chamber.

In another aspect, the system according to the invention optionally includes a separation vessel and/or a three-way connector.

In a further aspect, the invention includes methods of separating particles. In one of the methods according to the invention, the binding substance is mixed with a liquid carrying at least second and third particles to form a mixture. At least some of the ligands bind with the second particles to form groups of bound particles including the first and second particles. A portion of the binding substance is removed from the mixture and at least the liquid, third particles, and groups of bound particles flow into a fluid chamber. In the fluid chamber, the third particles and the groups of bound particles are separated according to differences in sedimentation velocity, and at least the liquid and at least a portion of the third particles are allowed to flow from the fluid chamber.

In an aspect of the invention, the removing of the portion of the binding substance includes gravity sedimentation, centrifugal separation, and/or filtering with a porous medium. Optionally, a diluting medium is added to the mixture to facilitate the removing.

In another method according to the invention, a saturated fluidized bed of particles is formed in the fluid chamber. The saturated fluidized bed of particles retains the groups of bound particles in the fluid chamber.

In yet another aspect of the invention, the mixture is allowed to incubate to increase the binding of the ligands and the second particles.

In the preferred practice of the invention, the ligands include at least one protein, antibody, chemical composition, and/or mixtures thereof. Preferably, the ligands include at least one antibody including anti-CD2, anti-CD3, anti-CD4, anti-CD8, anti-CD9, anti-CD10, anti-CD14, anti-CD15, anti-CD19, anti-CD20, anti-CD34, anti-CD38, anti-CMRF-44, anti-CD45, anti-CD56, anti-CD83, anti-glycophorin, anti-cytokeratin, anti-EPCAM, and/or combinations thereof.

In an additional aspect of the invention, the liquid carrying at least the second and third particles includes whole blood, blood components, a peripheral blood cell collection, a bone marrow blood cell collection, and/or blood components removed from an umbilical cord. Preferably, the first and second particles are different types of antigen-specific white blood cells.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate an embodiment of the invention and, together with the description, serve to explain the principles of the invention. In the drawings.

DESCRIPTION OF THE PREFERRED EMBODIMENTS

Figure 1:
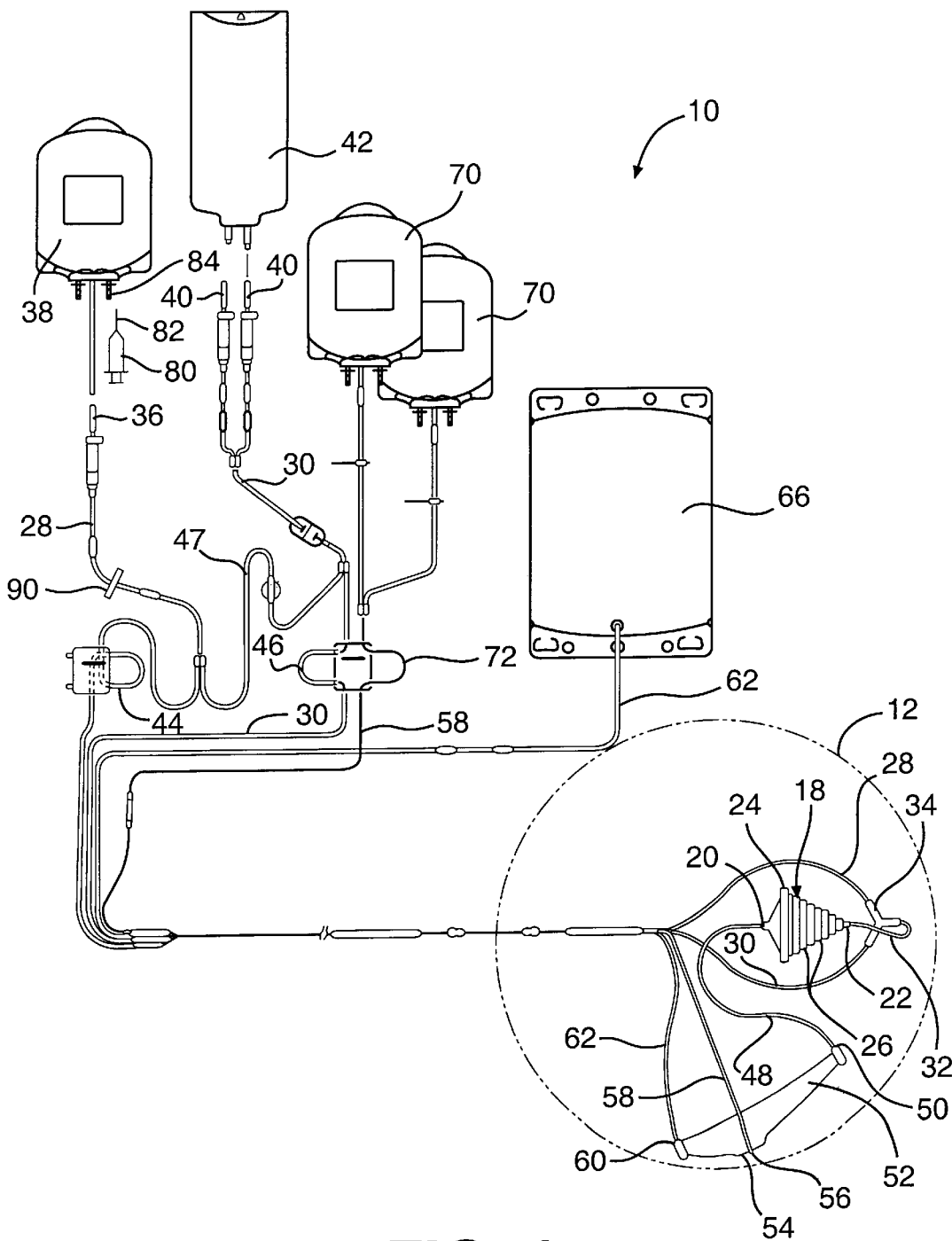
FIG. 1 is a schematic diagram of a particle separation system in accordance with an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

The embodiment of the present invention preferably includes a COBE® SPECTRA™ blood component centrifuge manufactured by Cobe Laboratories of Colorado. The COBE® SPECTRA™ centrifuge incorporates a one-omega/two-omega sealless tubing connection as disclosed in U.S. Pat. No. 4,425,112 to Ito, the entire disclosure of which is incorporated herein by reference. Although the embodiment of the invention is described in combination with the COBE® SPECTRA™ centrifuge, this reference is made for exemplary purposes only and is not intended to limit the invention in any sense.

As will be apparent to one having skill in the art, the present invention may be advantageously used in a variety of centrifuge devices commonly used to separate blood into its components. In particular, the present invention may be used with any centrifugal apparatus regardless of whether or not the apparatus employs a one-omega/two-omega sealless tubing connection.

As embodied herein and illustrated in FIG. 1, the present invention includes a particle separation system 10 having a centrifuge rotor 12. Preferably, the centrifuge rotor 12 is coupled to a motor (not shown) so that the centrifuge rotor 12 rotates about its axis of rotation A—A shown in FIG. 2.

Figure 2:
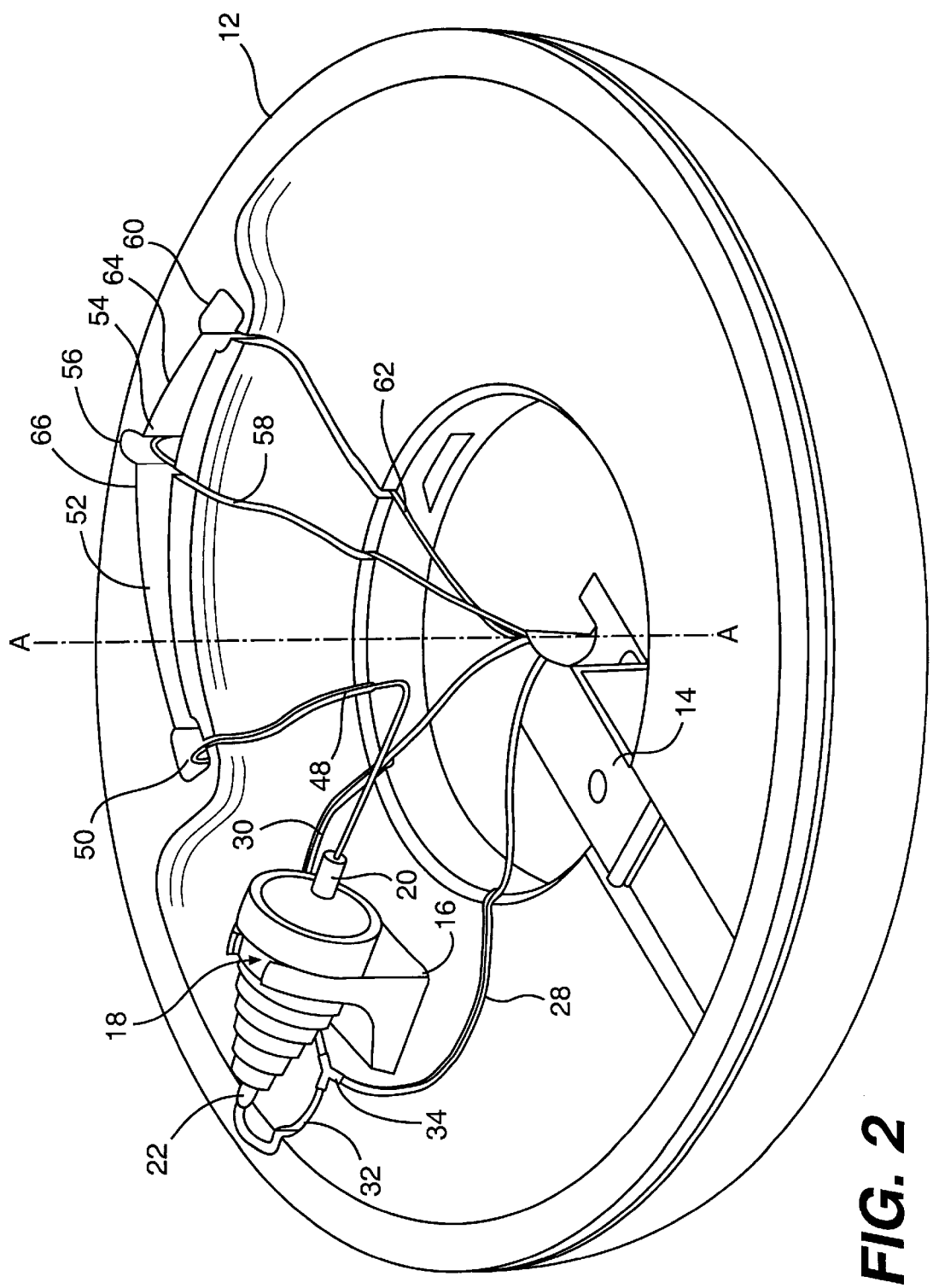
FIG. 2 is a perspective view of a fluid chamber and separation vessel mounted on a centrifuge rotor as depicted in FIG. 1.

As shown in FIG. 2, a holder 16 is provided on a top surface of the rotor 12. The holder 16 releasably holds a fluid chamber 18 on the rotor 12 such that an outlet 20 of the fluid chamber 18 is positioned closer to the axis of rotation A—A than an inlet 22 of the fluid chamber 18. Although the holder 16 retains the fluid chamber 18 on a top surface of the rotor 12, the fluid chamber 18 may also be secured to the rotor 12 at alternate locations, such as beneath the top surface of the rotor 12.

Figure 3:
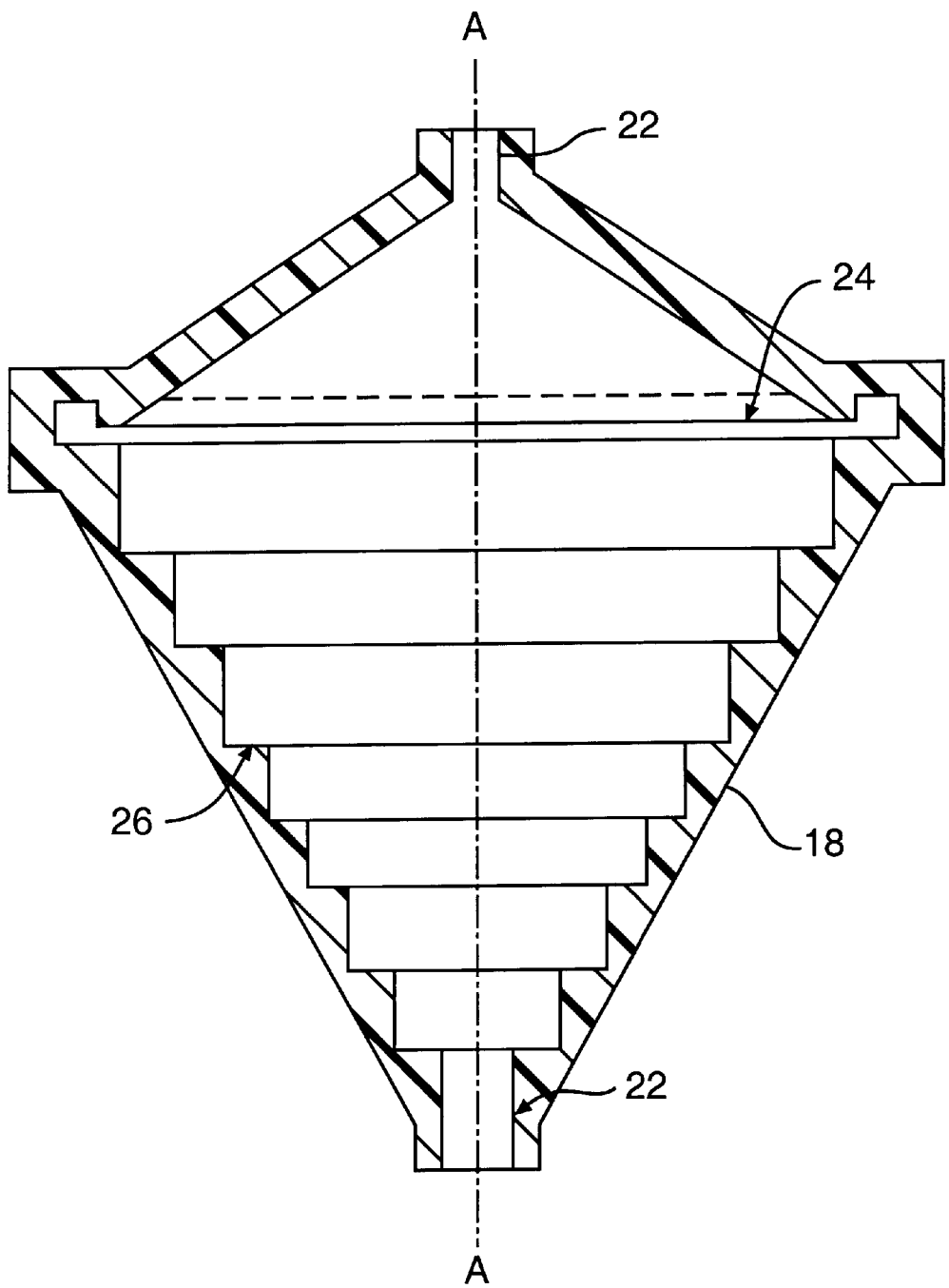
FIG. 3 is a schematic cross-sectional view of the fluid chamber.

The fluid chamber 18 is preferably constructed similar or identical to one of the fluid chambers disclosed in above-mentioned U.S. Pat. No. 5,674,173 and U.S. patent application Ser. No. 08/423,583 abandoned. As shown in FIGS. 1–3, the inlet 22 and outlet 20 of the fluid chamber 18 are arranged along a longitudinal axis of the fluid chamber 18. A wall of the fluid chamber 18 extends between the inlet 22 and outlet 20 thereby defining inlet 22, the outlet 20, and an interior of the fluid chamber 18.

The fluid chamber 18 includes two frustoconical shaped sections joined together at a maximum cross-sectional area of the fluid chamber 18. The interior of the fluid chamber 18 tapers (decreases in cross-section) from the maximum cross-sectional area in opposite directions toward the inlet 22 and the outlet 20. Although the fluid chamber 18 is depicted with two sections having frustoconical interior shapes, the interior of each section may be paraboloidal, or of any other shape having a major cross-sectional area greater than the inlet or outlet area.

The volume of the fluid chamber 18 should be at least large enough to accommodate the formation of a saturated fluidized particle bed (described below) for a particular range of flow rates, particle sizes, and rotational speeds of the centrifuge rotor 12. The fluid chamber 18 may be constructed from a unitary piece of plastic or from separate pieces joined together to form separate sections of the fluid chamber 18. The fluid chamber 18 may be formed of a transparent or translucent copolyester plastic, such as PETG, to allow viewing of the contents within the chamber interior with the aid of an optional strobe (not shown) during a separation procedure.

As shown in FIG. 3, a groove 24 is formed on an inner surface of the fluid chamber 18 at a position of the maximum cross-sectional area. The groove 24 is defined by top and bottom wall surfaces oriented substantially perpendicular to the longitudinal axis of the fluid chamber 18 and an inner surface of the fluid chamber 18 facing the longitudinal axis. Preferably, the groove 24 is annular, however, the groove 24 may also partially surround the longitudinal axis of the fluid chamber 18.

The groove 24 helps to reduce the effects of Coriolis jetting within the fluid chamber 18. Sudden increases in liquid flow rate during a particle separation procedure may limit the ability of the saturated fluidized particle bed to obstruct particle passage. Liquid flowing into the fluid chamber 18 may undergo a Coriolis jetting effect. This jetting flow reduces the filtration effectiveness of a saturated fluidized particle bed formed in the fluid chamber 18 because liquid and particles may pass between the saturated fluidized particle bed and an interior wall surface of the fluid chamber 18 rather than into the bed itself. The fluid chamber 18 including groove 24 counteracts these effects by channeling Coriolis jetting flow in a circumferential direction partially around the axis of fluid chamber 18. Therefore, the groove 24 improves the particle obstruction capability of the saturated bed, especially when liquid flow rates increase.

A plurality of steps 26 are preferably formed on an inner surface of the fluid chamber 18 between the maximum cross-section of the chamber 18 and the inlet 22. Each step 26 has a base surface oriented substantially perpendicular to the longitudinal axis of the fluid chamber 18, as well as a side surface positioned orthogonal to the base surface. Although FIG. 3 depicts a corner where the side surface and the base surface intersect, a concave groove may replace this corner. In a preferred embodiment, each step 26 is annular and surrounds the axis of the chamber 18 completely to bound a cylindrical shaped area. Alternatively, the steps 26 may partially surround the axis of the chamber 18.

The inclusion of steps 26 in the fluid chamber 18, also improves the particle obstruction characteristics of a saturated fluidized particle bed formed in the fluid chamber 18, in particular during increases in the rate of fluid flow. The steps 26 provide this improvement by providing momentum deflecting and redirecting surfaces to reduce Coriolis jetting in fluid chamber 18. When Coriolis jetting takes place, the liquid and particles of the jet travel along an interior surface of the fluid chamber 18 that faces the direction of centrifuge rotation. Therefore, the jet may transport particles between the fluid chamber interior surface and either a saturated fluidized particle bed or an elutriation field positioned in the fluid chamber 18. Thus, particles traveling in the jet may exit the fluid chamber 18 without being separated.

Steps 26 direct or alter the momentum of the Coriolis jet flow of liquid and particles generally in a circumferential direction about the axis of the fluid chamber 18. Thus, a substantial number of particles originally flowing in the jet must enter the saturated fluidized bed or elutriation field to be separated.

The groove 24 and steps 26 are provided to facilitate fluid flow rate increases, as well as to improve steady state performance of the fluid chamber 18. During blood component separation, the groove 24 and steps 26 greatly reduce the number of filtered cells that would otherwise bypass a saturated fluidized particle bed formed in the fluid chamber 18.

As shown in FIG. 1, the system 10 further includes a first conduit 28, second conduit 30, an inlet tubing 32 in fluid communication with the inlet 22 of the fluid chamber 18, and a three-way connector 34 having three legs for flow-connecting the first conduit 28, second conduit 30, and inlet tubing 32. The first conduit 28 includes a coupling 36 for flow-connecting the first conduit 28 with a first source 38 containing liquid carrying particles to be separated from one another. Likewise, the second conduit 30 includes couplings 40 for flow-connecting the second conduit 30 with a second source 42 containing a diluting liquid. The couplings 36 and 40 are preferably any type of common medical coupling devices, such as spikes or sterile tubing connectors.

As shown in FIG. 1, the first conduit 28 includes a first tubing loop 44, and the second conduit 30 includes a second tubing loop 46. During use, the first and second tubing loops 44 and 46 are mounted in peristaltic pumps (not shown) for respectively pumping the fluid to be separated and the diluting fluid from the first and second sources 38 and 42, respectively.

A line 47 is provided to continue the flow of diluting liquid into the first conduit 28 after the first source 38 and upper part of first conduit 28 are empty. Fluid communication of the upper part of first conduit 28 and the line 47 with the lower part of first conduit 28 is preferably controlled by pinch valves (not shown). The continued flow of diluting liquid into first conduit 28 allows flushing of any remaining particles in first conduit 28 into the fluid chamber 18, and allows the continued perfusion of the fluid chamber 18 with diluting liquid to continue the separation process in the fluid chamber 18.

Preferably, the density of the diluting fluid in the second source 42 is less than the density of both the particles and liquid in the first source 38. As described below, the fluid to be separated and diluting fluid mix with one another in the three-way connector 34 and the diluting fluid regulates (lowers) the overall density of substances flowing in the fluid chamber 18.

As shown in FIG. 1, the system 10 according to the invention, preferably includes a container 80. The container 80 contains a binding substance including particles and ligands attached to the particles in the binding substance. In addition, the container 80 also contains a carrier liquid, such as a liquid identical to the diluting liquid in the second source 42. As explained below, the binding substance in the container 80 is added to the liquid and particles in the first source 38, and at least some of the ligands bind with particular particles in the first source 38 to form groups of bound particles including at least one of the particles originally in the container 80 and at least one of the particles originally in the first source 38. These groups of bound particles are then separated from other particles in the fluid chamber 18 according to differences in sedimentation velocity, as explained below. Because each of the groups of particles has a greater sedimentation velocity than individual particles making up the groups, a saturated fluidized particle bed formed in the fluid chamber 18 retains the groups of particles in the fluid chamber 18, as also explained below.

Preferably, the particles in the container 80 are rigid, porous or non-porous, generally spherical beads. In a preferred embodiment, the particles in the container 80 are microspheres made of a polymeric material allowing the ligand to be bound or coated on the microsphere. Preferably, these particles are made of a polymeric material capable of binding with an antibody. For example, the particles in the container 80 are formed of polystyrene, polyacrylamide, latex, and/or polymethyl methacrylate.

In one preferred embodiment, the particles in the container 80 are SEPHADEX particles manufactured by PHARMACIA. SEPHADEX particles are polymerized dextran or dextran derivatives, for example, which are in the form of a beaded gel prepared by cross-linking dextran with epichlorohydrin under alkaline conditions. The size of SEPHADEX particles can be varied by selecting appropriate cross-linking conditions.

The particles in the container 80 could have many different shapes, sizes, densities. As mentioned above, the particles preferably have a generally spherical shape. The diameter of the particles is preferably greater than about 20 $\mu$m. For example, the diameter of the particles in the container 80 preferably is in a range of from about 20 $\mu$m to about 60 $\mu$m, and more preferably in a range of from about 20 $\mu$m to about 30 $\mu$m. Preferably, the density of the particles in the container 80 is in a range of from about 1.05 gm/mL to about 1.07 gm/mL, which is more than the density of the diluting liquid in the second source 42.

The ligands attached to the particles in the container 80 include one or more proteins, antibodies, chemical compositions, and/or mixtures thereof, which are capable of binding with particular particles in the first source 38. When the ligands include antibodies, there are many different types of antibodies that could be used. In a preferred embodiment, the ligands are antibodies selected from one or more of the following antibodies: anti-CD2, anti-CD3, anti-CD4, anti-CD8, anti-CD9, anti-CD10, anti-CD14, anti-CD15, anti-CD19, anti-CD20, anti-CD34, anti-CD38, anti-CMRF-44, anti-CD45, anti-CD56, anti-CD83, anti-glycophorin, anti-cytokeratin, anti-EPCAM, other cell phenotype antigens, and combinations thereof, for example. Individual particles in the container 80 may have two or more different types of antibodies attached thereto. In addition, different particles in the container 80 may have different types of attached antibodies.

Some examples of preferred proteins for the ligands include albumin and immunoglobulins. Preferred chemical composition for the ligands include poloxamers, such as PLURONIC®, and poly-lysine, for example.

Those skilled in the art should recognize that there are many different ways in which the ligands could be attached to the particles in the binding substance. For example, the ligands are attached to these particles by means of conjugation chemistry or surface coating.

Some examples of conventional attachment methods that could be used to attach the ligands to the binding substance particles are described in the following publications: "Tech. Note No. 13C, Covalent Coupling Protocols," Bangs Laboratories, Inc., Fishers, Ind.; "Chemical Coupling of Peptides and Proteins to Polysaccharides by Means of Cyanogen Halides," Rolf Axen et al., Nature, Vol. 214, Jun. 24, 1967, pgs. 1302–1304; "Immobilization of Ultra-thin Layer of Monoclonal Antibody on Glass Surface," Masanori Yoshioka et al., Journal of Chromatography, 566 (1991), pgs. 361–368; Pope et al., Bioconjugate Chemistry, Vol. 4 (1993), pgs. 166–171; Avidin-Biotin Chemistry: A Handbook, Savage et al., Pierce publishing (1992); Immobilized Affinity Ligand Techniques, Hemanson et al., Academic Press, Inc., New York (1992); and Antibodies: A Laboratory Manual, Harlow and Lane, Colorado Spring Harbor Lab (1988), the entire disclosures of which are incorporated herein by reference to provide further background information.

When the ligands are antibodies, the ligands can be attached to the particles in the container 80 by means of conjugation chemistry known to those skilled in the art. In one approach, the particles are coated with poly-l-lysine and the antibody is bound to the coated particle with glutaraldehyde. In another approach, particles formed from carbohydrate polymers such as dextran or dextran derivatives (e.g., aminoethyl-Sephadex, Sephadex, etc.) are activated with cyanogen halides to form cyanamide, iminocarbonic acid esters, or carbamic acid esters. A variety of bifunctional or hetero bifunctional cross-linking reagents may also be selected for this application. In addition, spacer groups could be used in these cross-linking agents to reduce steric hindrance and increase binding efficiency and capacity. Suitable spacer groups may include hydrophobic or hydrophilic groups such as alkanes ($C_n$) or polyethylene glycol ($-CH_2-O-CH_2-$)$_n$ (where n is an integer), respectively. In one embodiment, particle beads may be pre-activated by attaching substances with amino ($NH_2$), carboxy ($COOH$) or aldehyde ($CHO$) end termini.

In a preferred embodiment, the particles in the container 80 are treated to include Avidin—a factor occurring in the white portion of eggs of birds and amphibia and in the genital tract of animals, which is capable of binding with biotin a growth factor present in minute amounts in all living cells. Linkage could then be accomplished via attachment to biotinylated antibodies.

For example, the binding substance in the container 80 includes TOYO PEARL® HW 40S column packing particles (manufactured by SUPELCO, Inc.) conjugated with anti-CD8 antibodies and suspended in an electrolyte solution, such as ISOLYTE® pH 7.4 (Multi-Electrolyte Injection). Preferably, the particles have an average diameter of about 43.5 $\mu$m with a mode of about 45 $\mu$m and a range of about 32.5 $\mu$m to about 52.5 $\mu$m. There is preferably about 100 $\mu$g of antibody for each mL of particles. The ISOLYTE®S pH 7.4 is manufactured by McGraw, Inc. and has the following amounts of electrolyte in units of mEq/liter:

| $Na^+$ | 141 | $Mg^+$ | 3 | Phosphate | |
|---|---|---|---|---|---|
| $K^+$ | 5 | $Cl^-$ | 98 | ($HPO_4$) | 1 |
| | | Acetate | 27 | (0.5 mmole P/L) | |
| | | | | Gluconate | 23 |

Each 100 mL of ISOLYTE® contains Sodium Chloride USP 0.53 g, Sodium Gluconate USP 0.5 g, Sodium Acetate•3$H_2O$ USP 0.37 g, Potassium Chloride USP 0.037 g, Magnesium Chloride•6$H_2O$ USP 0.03 g, Dibasic Sodium Phosphate•7$H_2O$ USP 0.012 g, Monobasic Potassium Phosphate NF 0.00082 g, and Water for Injection USP qs. In addition, this substance may also include Glacial Acetic Acid USP or Sodium Hydroxide NF to adjust pH so that the pH is about 7.4. ISOLYTE® has a calculated Osmolarity of 295 mOsmo/liter, a density of 1.005 gm/ml at 25 degrees Celsius, and a viscosity of 1.02 cp at 22 degrees Celsius.

Preferably, the liquid and particles in the first source 38 are whole blood, blood removed from an umbilical cord, and/or blood components, such as a peripheral blood cell collection or bone marrow blood cell collection primarily including plasma, red blood cells, stem cells (CD34+ cells), and T-cells (CD2+ cells, CD3+ cells, CD4+ cells, and CD8+ cells) and also possibly including an amount of B-cells (CD9+ cells, CD10+ cells, and CD19+ cells), NK cells (CD56+ cells), monocytes (CD14+ cells), and other leukocytes (CD45+ cells, for example). Preferably, the blood components in the first source 38 include different antigen-specific white blood cells. For example, the blood components in the first source 38 preferably include at least two of the following types of antigen-specific white blood cell types: CD2+ cells, CD3+ cells, CD4+ cells, CD8+ cells CD9+ cells, CD10+ cells, CD19+ cells, and CD45+ cells. In addition, the first source 38 may also contain CD15+ cells, CD20+ cells, CD38+ cells, CMRF-44+ cells, CD83+ cells, glycophorin+ cells, cytokeratin+ cells, and/or EPCAM+ cells.

As explained below, the binding substance in the container 80 is added to the liquid and particles (i.e., blood components) in the first source 38. Groups of bound particles form in the resulting mixture when the ligands attached to the particles in the binding substance bind with specific particles originally in the first source 38. For example, when anti-CD2 is the ligand attached to the particles in the binding substance, the anti-CD2 binds with CD2+ cells, such as CD2+ T-cells, to form groups of particles each including at least one of the particles originally in the container 80 bound to at least one of the CD2+ cells originally in the first source 38. Groups of bound particles form in a similar manner when the binding substance includes other types of antibodies, proteins, and/or chemical compositions having different affinities for particular particles in the first source 38.

The container 80 containing the binding substance 80 could be packaged separate from the other structural components of the system 10. Alternatively, the container 80 containing the binding substance is packaged in a kit form along with some or all of the structural components of the system 10 shown in FIG. 1, except for the centrifuge rotor 12. Those skilled in the art should recognize that there are many different types of packages that could be used to contain these components.

As shown in FIG. 1, the container 80 itself is preferably a syringe barrel capable of being coupled to a syringe needle 82 or connector capable of being passed in a sealed fashion through a port 84 in the first source 38 to allow for mixing of the binding substance with the contents of the first source 38 when a plunger of the syringe barrel is pressed. Alternatively, the container 80 could be a vial, bottle, bag, or any other type of fluid containing structure capable of being placed in fluid communication with the first source 38. For example, the container 80 could be a pre-filled, sealed tubing segment coupled to the first source 38, which is capable of being placed in fluid communication with the first source 38 by opening a valve or seal. In another alternative embodiment, the container 80 is a sealed pre-filled bulb capable of being connected in a sterile manner to the port 84, so that the bulb could be squeezed to discharge its contents into the first source 38 prior to connecting the first source 38 to the first conduit 28. Preferably, the particular container 80 allows the system 10 to remain relatively closed and sterile.

In a preferred embodiment, the diluting liquid in the second source 42 is a solution including electrolytes. To ensure that the diluting solution is not detrimental to the blood components, the electrolyte solution has a pH of preferably from about 5.0 to about 8.0, more preferably from about 7.0 to about 7.8, and most preferably about 7.4. For example, the electrolyte solution is a conventional saline solution, lactated ringers solution, or dextrose saline solution having a pH of about 7.4. Preferably, the diluting liquid is the above-mentioned ISOLYTE®S pH 7.4 (Multi-Electrolyte Injection) manufactured by McGaw, Inc.

Optionally, an adhesion-reducing agent is added to the first source 38 or the second source 42. For example, liquid and particles in the first source 38 and/or the diluting liquid in the second source 42 include up to about 2% by weight of a polymer material for reducing adherence of the particles to one another, for reducing adherence of the particles to components of the system 10 and for reducing non-specific adherence of unintended cells to the particles. For example, this polymer material is a triblock, polyethylene oxide-polypropylene oxide-polyethylene oxide copolymer having the chemical formula $HO-(CH_2CH_2O)_A-(CHCH_3CH_2O)_B-(CH_2CH_2O)_A-H$, wherein A satisfies the expression $0 \leq A \leq 150$ and B satisfies the expression $0 \leq B \leq 100$. In a preferred embodiment, A is 75 or 76 and B is 30. For example, the polymer material is preferably a poloxamer, such as PLURONIC® F68 or PLURACARE® F68 Prill manufactured by BASF Corp. As described below, the use of these polymer materials improves particle separation in the fluid chamber 18 and increases the yield of separated particles, in particular, when the separated particles are small in number.

In another aspect of the invention, the particles in the container 80 are formed of a polymer co-extruded with the adhesion-reducing agent, or the particles themselves may be coated with a solution containing the adhesion-reducing agent so that the resulting exterior surface of the particles includes the adhesion-reducing agent to limit non-specific adherence (i.e., to limit undesired binding of the particles in the binding substance with particular particles in the first source 38). An example of a triblock copolymer suitable for application in this mode of the invention is a series of polymers prepared by Thoratec Laboratories, Berkeley, Calif. These polymers are designated as surface modifying agents (SMAs) and consist of polylactone-polysiloxane-polylactone copolymers in which the siloxane is dimethyl-siloxane and the lactone is caprolactone. Nominal molecular weights of the polysiloxane blocks range from 1000 to 5000. The nominal molecular weights of the caprolactone blocks range from 1000 to about 10,000. Preferred coating material is provided by SMA-422 or SMA-423 having polycaprolactone blocks of 2000 nominal molecular weight and polysiloxane blocks of 2000 or 3000 nominal molecular weight. Preferably, the particles in the container 80 are coated with (or formed of a polymer coextruded with) a coating material disclosed in U.S. Pat. No. 5,702,823, the disclosure of which is incorporated by reference in its entirety. In another preferred embodiment, the particles in the container 80 are coated with (or formed of a polymer coextruded with) poloxamer.

The liquid and particles (including the groups of particles) from the first source 38 and the diluting liquid from the second source 40 flow through the respective first conduit 28 and second conduit 30 to the three-way connector 34. These substances mix in the three-way connector 34 and flow through the inlet tubing 32 into the fluid chamber 18. In the fluid chamber 18, turning with rotor 12, the particles (including the groups of particles) separate according to differences in sedimentation velocity leaving faster sedimenting particles and groups of particles in the fluid chamber 18 and allowing slower sedimenting particles to flow from the fluid chamber 18, as described below. Because the groups of bound particles, formed as a result of mixing the binding substance in the container 80 with the contents of the first source 38, are larger in size than their individual particle constituents, the groups of particles behave like particles having a faster sedimentation velocity.

After the particles are separated in the fluid chamber 18, the liquid and particles having a relatively slower sedimentation velocity flow through the fluid chamber outlet 20 into tubing 48. As shown in FIGS. 1 and 2, the tubing 48 is connected to an inlet 50 of a separation vessel 52 mounted to the centrifuge rotor 12. As described below, the separation vessel 52 separates particles from liquid.

Adjacent to an outer portion of the centrifuge rotor 12, the separation vessel 52 has a collection well 54 for collecting particles flowing into the separation vessel 52. Rotation of centrifuge rotor 12 sediments particles into the collection well 54 while slower sedimenting liquid and possibly some slower sedimenting particles remain above a top boundary of the collection well 54.

The collection well 54 has a particle concentrate outlet 56 connected to a particle concentrate line 58. The particle concentrate line 58 removes particles retained in the collection well 54 along with a small portion of liquid. The separation vessel 52 also includes a liquid outlet 60 connected to a liquid outlet line 62. The liquid outlet line 62 removes liquid flowing above a top boundary of the collection well 54. In addition, the liquid outlet line 62 may remove some slower sedimenting particles flowing past the collection well 54.

Preferably, the liquid outlet 60 is located at or adjacent to one end of the separation vessel 52, and the inlet 50 is located at or adjacent to an opposite end of the separation vessel 52. This spacing ensures ample time for separation of particles from liquid, collection of a substantial number of particles in the collection well 54, and corresponding removal of a substantial number of particles through the particle concentrate line 58.

In the preferred embodiment shown in FIG. 2, the separation vessel 52 is placed in a groove 64 formed in the rotor 12. Preferably, the separation vessel 52 is a channel formed of a semi-rigid material so that a valley 66 in an outer wall of the groove 64 forms the collection well 54 when the separation vessel 52 expands in response to liquid and particles in the separation vessel 52 encountering centrifugal forces. As shown in FIG. 2, the top surface of the rotor 12 preferably includes retainer grooves for receiving the first and second conduits 28 and 30, three-way connector 34, inlet tubing 32, tubing 48, particle concentrate line 58, and liquid outlet line 62.

As shown in FIG. 1, the liquid outlet line 62 is fluidly coupled to a liquid collection container 66 for collecting liquid removed from the separation vessel 52, and the particle concentrate line 58 is fluidly coupled to one or more particle collection containers 70 for collecting particles removed from the separation vessel 52. Preferably, the particle concentrate line 58 includes a tubing loop 72 capable of being mounted in a peristaltic pump for pumping particles through the particle concentrate line 58. The pump for tubing loop 72 regulates the flow rate and concentration of particles in particle concentrate line 58. To control flow rates of substances and rotational speed of the rotor 12 during operation of the system 10, a controller (not shown) controls pumps (not shown) for pumping substances through the first conduit 28, second conduit 30, and particle concentrate line 58, and controls a motor (not shown) for rotating the centrifuge rotor 12.

A preferred method of separating components of blood is discussed below with reference to FIGS. 1–4. Although the invention is described in connection with a blood component separation process and in connection with the structure shown in FIGS. 1–4, it should be understood that the invention in its broadest sense is not so limited. The invention may be used to separate a number of different types of particles, and many different types of structural arrangements could be used to practice the method according to the invention.

Initially, peripheral blood or bone marrow blood is collected from a patient and this blood is purified in a centrifugal separation process to isolate what is known as a peripheral blood cell collection or bone marrow blood cell collection, respectively. During this initial centrifugation process, platelet rich plasma, a portion of the red blood cells, and more dense white blood cells are separated from the blood to obtain a peripheral blood cell collection or bone marrow blood cell collection primarily including plasma, red blood cells, stem cells (CD34+ cells), and T cells (CD2+ cells, CD3+ cells, CD4+ cells, and CD8+ cells). In addition, this collection most likely includes some platelets, B-cells (CD9+ cells, CD10+ cells, and CD19+ cells), NK cells (CD56+ cells), monocytes (CD14+ cells), and other leukocytes (CD45+ cells, for example). As described in more detail below and shown in FIG. 4, particular particles, such as red blood cells "R", are used to form a saturated fluidized particle bed in the fluid chamber 18. If the number of red blood cells "R" in the blood cell collection is insufficient to form the saturated bed, additional red blood cells are preferably added to the first source 38 so that the number of red blood cells exceeds the number of other particles in the first source 38.

The initial separation of the peripheral blood or bone marrow blood is preferably performed on a centrifuge (not shown) separate from the system 10, such as a dual stage or single stage centrifugal separator. In an alternative embodiment, the centrifuge rotor 12 may include structure, such as generally annular channel fit in a groove on the rotor 12, for providing initial blood component separation on the centrifuge rotor 12, as disclosed in above-referenced U.S. Pat. No. 5,674,173 and U.S. patent application Ser. No. 08/423,583, abandoned.

The separated peripheral blood cell collection or bone marrow blood cell collection is placed in the first source 38 shown in FIG. 1. Then, the binding substance in the container 80 is added to the first source 38 to form a mixture including the original contents of the first source 38 and the original contents of the container 80. When the container 80 is a syringe, as shown in FIG. 1, the binding substance is added to the first source 38 by inserting the needle 82 in the port 84 and pressing a plunger of the syringe.

As the binding substance 38 mixes with the blood components in the first source 38, at least some of the ligands attached to the particles of the binding substance begin to bind to specific particles of the blood components depending upon the particular type of ligands in the binding substance. For example, when the ligands in the binding substance include anti-CD8, the ligands bind the particles of the binding substance to CD8+ T-cells in the first source 38 to form groups of bound particles including the particles of the binding substance and the CD8+ T-cells. As explained below, this enables the CD8+ T-cells to be separated from red blood cells and from other T-cells, such as CD4+ T-cells, which have a size and density similar to that of the CD8+ T-cells.

To increase the binding of the ligands with the specific blood components, the mixture of the binding substance and the blood components is preferably allowed to incubate for a period of time before this mixture is separated in the fluid chamber 18, as described below. For example, the mixture is preferably allowed to incubate for at least about one and one half hours. During the incubation, the mixture is preferably agitated to further increase the binding of the ligands with the blood components. The mixture could be agitated in many different ways, such as by stirring the mixture or vibrating the mixture. Although incubation is preferred in most cases, it may not be required in some particular particle separation procedures.

After a significant number of the particles and ligands of the binding substance are bound to the specific blood components in the first source 38, an initial separation is preferably performed to remove from the mixture a significant number of the unbound particles of the binding substance and possibly some bound groups of particles. The initial separation is preferred (but not always required) because it reduces the amount of binding substance particles ending up in the blood components separated in the fluid chamber 18, as described below. In addition, the initial separation ensures that the particles of the binding substance and groups of bound particles do not form a saturated fluidized particle bed in the fluid chamber 18. This initial separation could be performed in a number of different ways. In one preferred way of performing the initial separation, some of the groups of bound particles and some or all of the particles of the binding substance that are not bound to blood components are allowed to sediment in the mixture under the influence of gravity, without agitating the mixture. To make the mixture less viscous and thereby facilitate the gravity sedimentation, a diluting medium, such as the diluting liquid in the second source 42, is preferably added to the mixture prior to the gravity sedimentation. For example, the mixture could be diluted so that the ratio of diluting medium to the original mixture is about 4 to 1 by volume.

After the gravity sedimentation of the unbound particles of the binding substance and at least some of the bound groups of particles, the sediment is separated from the remainder of the mixture (the supernatant) residing above the sediment so that this remainder of the mixture may be further separated in the fluid chamber 18. For example, the remainder of the mixture is preferably decanted from the sediment and placed in the first source 38. Optionally, a conventional plasma expresser could be used to separate the sediment and the supernatant.

There are other ways in which the groups of bound particles and binding-substance particles that lack binding to blood components are capable being removed from the mixture. In one alternative method, some of the groups of bound particles and binding-substance particles are separated from the mixture centrifugally by performing a separation procedure on a conventional centrifuge. To facilitate the centrifugal separation, diluting medium is preferably added to the mixture.

Rather than performing gravity sedimentation or centrifugal separation, the bound-particle groups and binding-substance particles are alternatively separated from the remainder of the mixture by passing the mixture through a porous filter medium having a predetermined pore or mesh size configured to remove the particle groups and the binding-substance particles. For example, as shown in FIG. 1, the system 10 includes an optional filter 90 on the first conduit 28 for filtering bound-particle groups and binding-substance particles flowing through the first conduit 28. The filter 90 preferably has a polymeric, porous membrane, such as the Cell Microsieves® filter of BioDesign Inc., Carmel, N.Y. Although the filter 90 is preferably upstream of the fluid chamber 18, the filter 90 or a filter similar to the filter 90 could also be positioned in the system 10 downstream of the fluid chamber 18.

After optionally removing some of the bound particle groups and the binding substance particles from the mixture in the first source 38, the first source 38 is coupled to the first conduit 28. In addition, the second source 42 containing the diluting liquid is coupled to the second conduit 30. The centrifuge rotor 12 is rotated about the axis of rotation A—A, and the blood components, bound groups of particles, and diluting liquid are pumped from the first and second sources 38 and 42 and through the first and second conduits 28 and 30, respectively.

For example, the centrifuge rotor 12 is rotated at a speed of about 2,400 RPM to generate about 776 g at the fluid chamber inlet 20 and about 466 g at the fluid chamber outlet 22. If possible, the highest feasible rotational speed of rotor 12 is used to maximize the dynamic range of flow rates used in the process. The equilibrium flow rates are related to the square of the rotational speed.

As the blood components, bound groups of particles, and diluting liquid flow into the three-way connector 34, they mix with one another and flow into the fluid chamber 18 via the inlet tubing 32. Rotation of the centrifuge rotor 12 and the flow rate of substances entering the fluid chamber 18 are controlled to accumulate particles in the fluid chamber 18, while liquids, such as the plasma and diluting liquid flow from the fluid chamber 18. As shown schematically in FIG. 4, a fluidized bed of particles, including at least red blood cells "R," for example, eventually forms in the largest cross-sectional portion of the fluid chamber 18. In addition, the fluidized bed of particles also may include some T-cells "T" that do not form the bound groups of particles. When more red blood cells "R" and T-cells "T" flow into the particle bed, the bed reaches a state of saturation to become a saturated fluidized bed of particles.

Figure 4:
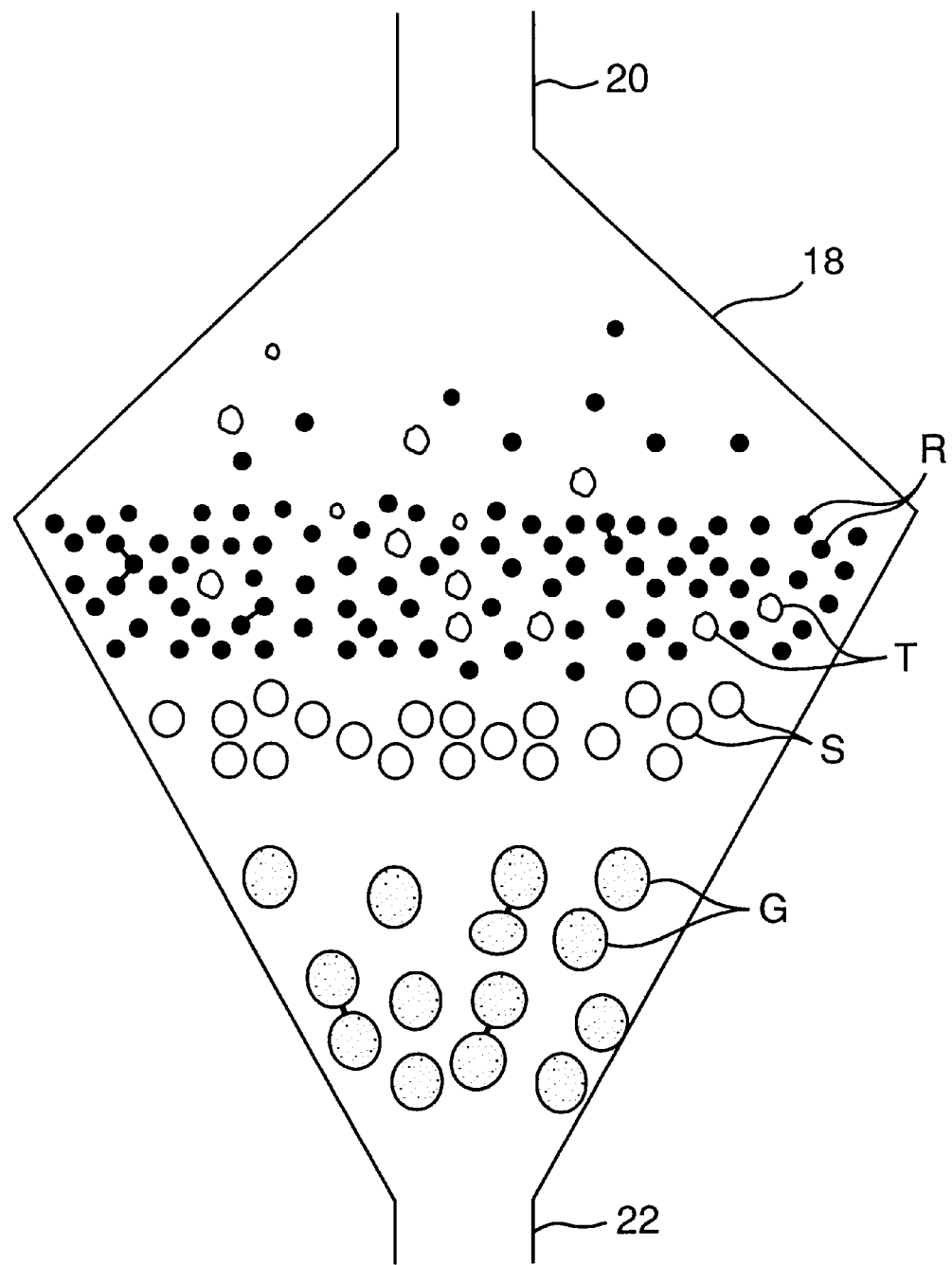
FIG. 4 is a schematic view of a saturated fluidized particle bed formed in the fluid chamber of FIG. 1 during a blood component separation procedure.

As shown in FIG. 4, plasma, diluting liquid, and any slower sedimenting particles, such as platelets, flow through the saturated particle bed, while the particle bed retains relatively faster sedimenting stem cells "S" and groups of bound particles "G" in a portion of the fluid chamber 18 located between the bed and the fluid chamber inlet 22. The stem cells "S" reside just below the saturated fluidized bed and the faster sedimenting particle groups "G" reside closer to the inlet 22. In addition to the stem cells "S" and particle groups "G," the saturated fluidized particle bed may also retain all or a substantial number of other blood particles having a sedimentation velocity faster than that of the red blood cells "R." Preferably, the saturated fluidized particle bed also retains any unbound particles of the binding substance which were not removed during the initial separation of these particles from the substances in the first source 38.

In the preferred practice of the present invention, both the T-cells "T" in the saturated fluidized particle bed and the blood component particles in the bound particle groups "G" are white blood cells. In addition, the slower sedimenting particles flowing through the saturated fluidized particle bed may also include white blood cells, platelets, proteins, drugs, cytokines, and combinations thereof, for example, if such particles were in the first source 38. For example, when the ligands in the binding substance include antigen-CD8, CD8+ T-cells form part of the particle groups "G" retained by the saturated fluidized particle bed, and other T-cells, such as CD4+ T-cells, form at least part of the saturated fluidized bed and/or flow through the particle bed. This allows for the CD8+ T-cells to be separated from the CD4+ T-cells.

As red blood cells "R" and T-cells "T" continue to flow into the fluid chamber 18 and enter the saturated fluidized bed, the red blood cells "R" and T-cells "T" flow from the outlet 20. Because the fluidized particle bed is saturated, the rate at which red blood cells and T-cells "T" enter the inlet 22 equals the rate at which red blood cells "R" and T-cells "T" pass through the outlet 20. The flow of red blood cells "R" and T-cells "T" also carries with it some portion of the number of stem cells "S." Generally, a larger number of stem cells "S" exit the fluid chamber 18 when the starting number of red blood "R" cells and/or white blood cells is greater.

Since the diluting liquid has a density less than that of the plasma and other blood components flowing through the first conduit 28, the mixing of the diluting liquid, blood components, and bound particle groups in the three-way connector 34 lowers the overall density of the combined suspension of the liquids and particles in the fluid chamber 18. This reduces Coriolis jetting of the plasma and diluting liquid flowing through the fluid chamber 18 because the composite liquid has a density closer to that of the overall density of substances in the fluid chamber 18. In other words, making the overall density of substances in the fluid chamber 18 closer to the density of liquids entering the fluid chamber 18 reduces buoyancy forces tending to move the liquid toward the fluid chamber outlet 20.

In contrast, when the overall density of substances in the fluid chamber 18 is relatively high, buoyancy forces cause the lower density liquids to flow in a Coriolis jet along the fluid chamber's inner wall surface facing the direction of rotation of the rotor 12. This Coriolis jetting of the liquids carries faster sedimenting particles, such as the bound particle groups "G," toward the fluid chamber outlet 20 and thereby allows these particles to flow from the fluid chamber 18 and to mix with the slower sedimenting particles, such as red blood cells, T-cells, and stem cells. Because Coriolis jetting is reduced, more of the faster sedimenting bound particle groups "G" can be separated from the blood component particles.

Although the use of the diluting liquid is preferred, it is not required in order to separate particles and particle groups in the fluid chamber 18. Diluting the blood components with diluting fluid allows for the blood components and bound particle groups in the first conduit 38 to be pumped into the fluid chamber 18 and separated at a faster, more constant flow rate while particles are entering the fluid chamber 18 and afterward while pure diluting fluid is entering the fluid chamber 18. In contrast, when the blood components and particle groups are separated in the fluid chamber 18 without dilution, the viscosity and density of plasma do not allow such high flow rates. In addition, some of the bound particle groups may be forced or carried through the fluid chamber outlet 20, due to high suspension densities in the chamber 18 combined with the low density of pure diluting liquid following the last cells into the chamber 18.

During particle separation, the pumping of the blood components and bound particle groups in the first conduit 28 and the pumping of the diluting liquid in the second conduit 30 are controlled so that the flow rate of diluting fluid exceeds the flow rate of blood components and bound particle groups. For example, the ratio of the flow rate of diluting liquid to the combined flow rate of blood components and bound particle groups is preferably from about 1 to about 20, more preferably from about 2 to about 8, and most preferably about 6. Highly diluting the blood components with the diluting liquid allows for separation of the bound particle groups and blood particles at an increased flow rate.

Although the diluting liquid, blood components, and bound particle particles are preferably mixed in the three-way connector 34 during a particle separation procedure, other mixing configurations are possible. For example the fluid chamber 18 could be modified to include separate inlets for blood components and particle groups and for diluting liquid. In addition, the diluting liquid could be added only during certain portions of the separation process.

Eventually all of the blood components and groups of bound particles flow from the first source 38 to the fluid chamber 18, and the first source 38 reaches an empty state. Thereafter, a quantity of the diluting liquid alone is passed into the fluid chamber 18 to reduce the overall density of substances in the fluid chamber 18 even further and thereby reduce Coriolis jetting. For example, 250 ml of pure diluting liquid is passed into the fluid chamber 18 after the first source 38 is empty. The diluting liquid flushes some of the desired particles from the fluid chamber 18.

After the blood components and particle groups become depleted from the first source 38, and diluting liquid has flushed a sufficient number of desired cells from the chamber 18, to further lower the suspension density in the chamber 18, the remaining stem cells "S" and other desired particles in the fluid chamber 18 are harvested. During harvesting, the flow rate of the diluting fluid is increased gradually in increments so that particles having relatively slower sedimentation velocities are flushed from the fluid chamber 18. The flow velocity of diluting liquid is preferably increased in a relatively slow and gradual fashion and at a relatively constant (linear) rate. Slowly increasing the flow rate of diluting liquid in this manner, reduces the likelihood of Coriolis jetting caused by sudden flow rate increases.

As harvesting continues, the flow rate of diluting liquid is increased until it is about 50% to about 100% greater than the combined flow rate of blood components, particle groups, and diluting liquid prior to harvesting, for example. Preferably, a fluidized bed of particles remains throughout a substantial portion of the harvesting. The reduced overall density of substances in the fluid chamber 18 reduces the likelihood of Coriolis jetting during particle harvesting. Preferably, the flow rate increase continues until just before bound particle groups "G" start to emerge from the fluid chamber outlet 20.

The diluting liquid, plasma, red blood cells, T-cells, stem cells, and any other materials flowing from the fluid chamber outlet 20 pass through the intermediate tubing 48 to the inlet 50 of the separation vessel 52. In the separation vessel 52, centrifugal force caused by rotation of the rotor 12 retains the particles in the collection well 54, while the diluting liquid and plasma flow through the liquid outlet 60 and liquid outlet line 62. This separates the red blood cells, stem cells, and other particles from the diluting liquid and plasma.

The particles and a portion of the liquids flow through the particle concentrate line 58 to one or more particle collection containers 70, and the diluting liquid and plasma flow through the liquid collection line 62 to the liquid collection container 66. After the first source 38 is empty, and desired cells have been recovered into collection containers 70, a procedurist terminates rotation of rotor 12 and optionally removes the bound particle groups "G" and any other faster sedimenting particles from the fluid chamber 18 for testing or other purposes.

When the blood components in the first source 38 and/or the diluting liquid in the second source 42 include the above-mentioned polymer having the chemical formula $HO-(CH_2CH_2O)_A-(CHCH_3CH_2O)_B-(CH_2CH_2O)_A-$ H, the polymer reduces adherence of at least some of the particles, such as the red blood cells, T cells, and stem cells. In particular, the polymer reduces rouleau (linking) of the red blood cells to one another. This improves separation of the particles in the fluid chamber 18 because the individual particles do not adhere to one another or to the components of the system 10. Therefore, the use of the polymer increases the number of red blood cells, T cells, and/or stem cells collected in the particle containers 70, especially when the first source 38 initially includes a small number of these particles.

In an alternative method according to the invention, particles are separated in the fluid chamber 18 according to differences in sedimentation velocity without forming a saturated fluidized bed of particles. For example, the particles could be separated in the fluid chamber by elutriation by using plasma in first source 38 and diluting liquid in second source 42, for example, as an elutriation fluid medium. In another aspect of the invention, the above-mentioned triblock polymer can be used to improve particle separation when the particles are separated without forming a saturated fluidized particle bed.

In another alternative method according to the invention, the substances flowing from the fluid chamber outlet 20 are monitored to detect binding substance particles, and these binding substance particles are removed. For example, a filter having a mesh size preventing passage of large substances and permitting passage of smaller particles could be placed in-line downstream from the fluid chamber 18 to filter the binding substance particles. In addition, a dye, could be added to the binding substance particles and a monitor for detecting the dye could be positioned downstream from the fluid chamber outlet 20, for example.

When the present invention is used to separate particles including red blood cells, the red blood cells act as individual, independent, sedimenting particles without significant rouleau of the red blood cells. The use of the diluting liquid reduces the density and viscosity of substances flowing in the fluid chamber 18, and thereby limits the occurrence of red blood cell rouleau. Adding the above-mentioned triblock copolymer to the substances flowing in the fluid chamber 18 also limits the tendency of red blood cell rouleau by reducing adhesion of red blood cells to one another. Because rouleau of the red blood cells is reduced, the red blood cells form at least part of the saturated fluidized particle bed rather than acting like faster sedimenting particles.

In the present invention, the red blood cells in the saturated bed block passage of faster sedimenting groups of bound particles. Because the bed forming red blood cells behave as if they have a faster sedimentation velocity than stem cells, the red blood cells permit stem cells to pass through the saturated bed. Stem cell recovery and particle conjugate filtering are improved when large numbers of red blood cells are used. In contrast, large numbers of red blood cells inhibit separation of stem cells and larger cells in most, if not all, conventional elutriation processes.

Although the saturated fluidized bed preferably includes at least red blood cells, the saturated fluidized bed may include other types of particles. For example, beads, which are formed of particular materials, such as SEPHADEX or polyacrylamide, and which have a predetermined size and density, could be added to the first source 38 and used to form a saturated fluidized bed alone or in combination with red blood cells.

Experiments were performed to show the effectiveness of initially separating some groups of bound particles before performing separation in the fluid chamber 18. These experiments used samples of whole blood having a ratio of the number of CD4+ cells to the number of CD8+ cells of 2.2, as determined by conventional hematology and flow cytometry analysis. In the tests, various amounts of binding particles having attached anti-CD8 antibody were added to the samples. The binding particles were the above-mentioned TOYOPEARL® HW40S particles conjugated with anti-CD8 antibodies and suspended in the above mentioned ISOLYTE®, pH 7.4.

In the experiments, different amounts of the binding particles were added to the whole blood samples after determining the number of CD8+ cells in the samples. The samples were allowed to incubate for 1.5 hours while the samples were agitated. Thereafter, the samples were diluted by adding phosphine buffered saline solution in a volume ratio of 8 parts of the saline to 1 part of the sample. Each diluted sample was allowed to sediment under the influence of normal gravity for 20 minutes at room temperature to sediment binding particles and bound CD8+ cell-binding particle groups. The saline solution added after incubation facilitated this sedimentation. Then, an aliquot of supernatant was removed from each of the samples and tested to determine the ratio of the number of CD4+ cells to the number of CD8+ cells present in each aliquot.

The table set forth below shows the results of the experiments for different trials A, B, C, D, E, and F.

| TRIAL | Ratio of the Number of Added Binding Particles to the Original Number of CD8+ cells in the sample | Ratio of the number of CD4+ cells to the Number of CD8+ cells in the supernatant | Ratio of Final CD4+/CD8+ to Inital CD4+/CD8+ [3rd column value ÷ 2.2] |
|---|---|---|---|
| A | 0.1 | 2.9 | 1.3 |
| B | 0.5 | 3.1 | 1.4 |
| C | 1 | 3.7 | 1.7 |
| D | 3 | 14.2 | 8.9 |
| E | 20 | 21.3 | 9.7 |
| F | 40 | 18.7 | 8.5 |

In the table, the second column shows the ratio of the number of binding particles added to the sample prior to incubation to the number of CD8+ cells in the original whole blood sample for each Trial A–F. The third column shows the ratio of the number of CD4+ cells to the number of CD8+ cells in the supernatant for each trial A–E. The fourth column is the ratio of 1) the CD4+/CD8+ ratio in column 3 to 2) the original CD4+/CD8+ ratio in the whole blood, 2.2.

Figure 5:
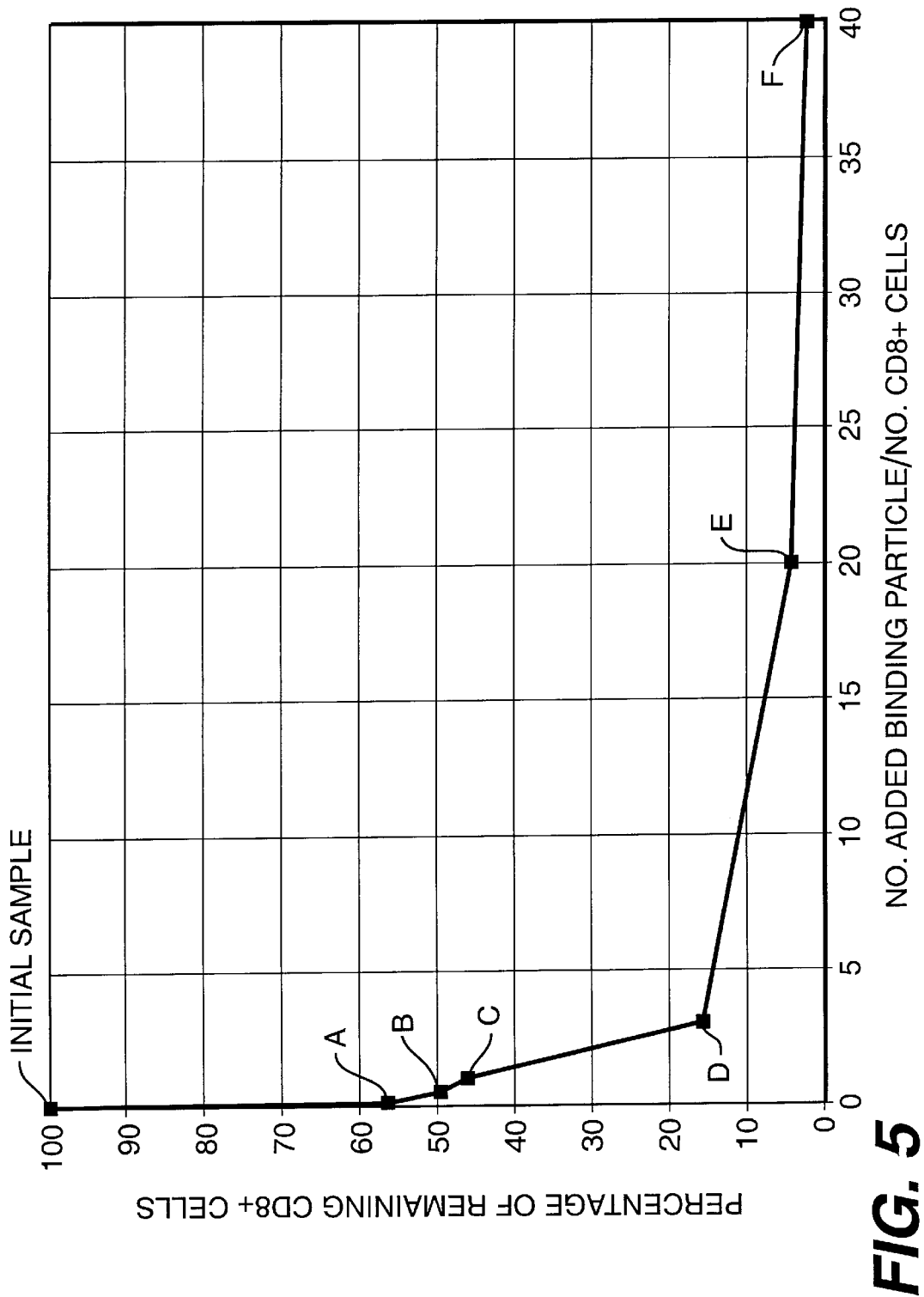
FIG. 5 is graph showing the results of experiments related to initial separation of bound particle groups.

FIG. 5 is a graph in which the abscissa (X-Axis) represents the ratio of the number of added binding particles to the original number of CD8+ cells in the sample (the second column of the above table), and the ordinate (Y-Axis) represents the percentage of CD8+ cells remaining in the supernatant as compared to the initial whole blood sample. Data points for the original whole blood sample and for the Trials A–F are plotted on the graph of FIG. 5.

The Experiment trials A–F show that the initial separation of the bound particle groups is effective to initially reduce the number of CD8+ cells, such as CD8+ T cells, without significant reduction of the number of CD4+ cells, for example (where the ligand is anti-CD8). This data further shows that as the number of binding particles increases, a point is reached where adding more binding particles does not significantly improve the initial particle separation. In some circumstances, the determination of the optimum number of binding particles for a particular procedure is preferred to reduce cost and to ensure that the binding particles alone do not form a saturated fluidized particle bed in the fluid chamber 18.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A method of separating particles, comprising:
    mixing a binding substance including first particles and ligands attached to the first particles with a liquid carrying at least second and third particles to form a mixture, at least some of the ligands binding with the second particles to form groups of bound particles including the first and second particles;
    removing a portion of the binding substance from the mixture, the portion of the binding substance removed from the mixture including first particles having attached ligands lacking binding to the second particles;
    rotating a fluid chamber about an axis of rotation;
    flowing at least the liquid, third particles, and groups of bound particles into the fluid chamber;
    separating in the fluid chamber the third particles and the groups of bound particles according to differences in sedimentation velocity; and
    allowing at least the liquid and at least a portion of the third particles to flow from the fluid chamber.

2. The method of claim 1, wherein the separating includes forming a saturated fluidized bed of particles in the fluid chamber, the saturated fluidized bed of particles retaining groups of bound particles in the fluid chamber.

3. The method of claim 2, wherein the particles forming the saturated fluidized bed include at least one of red blood cells and beads having a predetermined size.

4. The method of claim 2, wherein the particles forming the saturated fluidized bed include at least the third particles.

5. The method of claim 1, wherein the separating includes separating the third particles and the groups of bound particles by elutriation.

6. The method of claim 1, further comprising allowing incubation of the mixture to increase the binding of the ligands with the second particles.

7. The method of claim 6, further comprising agitating the mixture during the incubation to further increase the binding of the ligands with the second particles.

8. The method of claim 1, wherein the removing includes removing some of the groups of bound particles from the mixture.

9. The method of claim 1, wherein the removing includes allowing gravity sedimentation in the mixture of at least the first particles having attached ligands lacking binding to the second particles, and separating at least the sediment from the remainder of the mixture.

10. The method of claim 9, wherein the method further comprises adding a diluting medium to the mixture to facilitate the gravity sedimentation.

11. The method of claim 9, wherein the separating of the sediment from the remainder of the mixture includes decanting the remainder of the mixture from the sediment.

12. The method of claim 1, wherein the removing includes centrifugally separating at least the portion of the binding substance from the remainder of the mixture on a centrifuge.

13. The method of claim 12, wherein the method further comprises adding a diluting medium to the mixture to facilitate the centrifugal separation.

14. The method of claim 1, wherein the removing includes passing the mixture through a porous medium to filter at least the portion of the binding substance from the remainder of the mixture.

15. The method of claim 1, wherein the liquid carrying at least the second and third particles includes at least one of the group consisting of: whole blood, blood components, a peripheral blood cell collection, a bone marrow blood cell collection, and blood components removed from an umbilical cord.

16. The method of claim 1, wherein the liquid includes plasma.

17. The method of claim 1, wherein the ligands include at least one of the group consisting of: a protein, an antibody, a chemical composition, and mixtures thereof.

18. The method of claim 1, wherein the ligands include at least one antibody selected from the group consisting of: anti-CD2, anti-CD3, anti-CD4, anti-CD8, anti-CD9, anti-CD10, anti-CD14, anti-CD15, anti-CD19, anti-CD20, anti-CD34, anti-CD38, anti-CMRF-44, anti-CD45, anti-CD56, anti-CD83, anti-glycophorin, anti-cytokeratin, anti-EPCAM, and combinations thereof.

19. The method of claim 1, wherein the ligands include at least one protein selected from the group consisting of: albumin and immunoglobulin.

20. The method of claim 1, wherein the ligands include at least one of the group consisting of: poloxamers and polylysine.

21. The method of claim 1, wherein an exterior surface of the first particles includes at least one of the group consisting of a surface modifying agent and poloxamer.

22. The method of claim 21, wherein the exterior surface of the first particles includes a surface modifying agent coomprising a polylactone-polysiloxane-polylactone triblock copolymer.

23. The method of claim 1, wherein the first particles are rigid, generally spherical beads.

24. The method of claim 1, wherein the second particles include at least one of the group consisting of: antigen-specific white blood cells, CD2+ cells, CD3+ cells, CD4+ cells, CD8+ cells, CD9+ cells, CD10+ cells, CD14+ cells, CD15+ cells, CD19+ cells, CD20+ cells, CD34+ cells, CD38+ cells, CMRF-44+ cells, CD45+ cells, CD56+ cells, CD83+ cells, glycophorin+ cells, cytokeratin+ cells, EPCAM+ cells, and combinations thereof.

25. The method of claim 1, wherein the third particles include at least one of the group consisting of: red blood cells, antigen-specific white blood cells, platelets, proteins, drugs, cytokines, and combinations thereof.

26. The method of claim 1, wherein the second and third particles include different types of antigen-specific white blood cells.

27. The method of claim 1, further comprising
    passing into the fluid chamber a diluting liquid, the diluting liquid having a density less than that of the first, second, and third particles so that the diluting liquid reduces an overall density of substances in the fluid chamber and thereby limits Coriolis jetting of at least one of the liquid carrying the particles and the diluting liquid in the fluid chamber; and
    allowing the diluting liquid to flow from the fluid chamber.

28. The method of claim 27, further comprising mixing the liquid carrying particles and the diluting liquid so that at least portions of the passing and flowing are performed simultaneously.

29. The method of claim 1, further comprising flowing the liquid and third particles from the fluid chamber into a separation vessel, separating the third particles from the liquid in the separation vessel, and collecting at least the third particles in a container.

30. The method of claim 1, further comprising adding an adhesion-reducing agent to the liquid carrying particles.

31. The method of claim 1 wherein the first particles include a dye, and wherein the method further comprises monitoring substances flowing from an outlet of the fluid chamber to detect the dye.

32. The method of claim 1, further comprising monitoring substances flowing from an outlet of the fluid chamber to detect first particles flowing from the outlet, and removing the first particles from the substances.

33. A method of separating particles, comprising:
mixing a binding substance including first particles and ligands attached to the first particles with a liquid carrying at least second and third particles to form a mixture, at least some of the ligands binding with the second particles to form groups of bound particles including the first and second particles;
rotating a fluid chamber about an axis of rotation;
flowing at least the liquid, third particles, and groups of bound particles into the fluid chamber;
forming, in the fluid chamber, a saturated fluidized bed of particles, the saturated fluidized bed of particles retaining the groups of bound particles in the fluid chamber; and
allowing at least the liquid and at least a portion of the third particles to flow from the fluid chamber.

34. The method of claim 33, wherein the particles forming the saturated fluidized bed include at least one of red blood cells and beads having a predetermined size.

35. The method of claim 33, wherein the particles forming the saturated fluidized bed include at least the third particles.

36. The method of claim 33, further comprising allowing incubation of the mixture to increase the binding of the ligands with the second particles.

37. The method of claim 33, further comprising agitating the mixture during the incubation to further increase the binding of the ligands with the second particles.

38. The method of claim 33, wherein the liquid carrying at least the second and third particles includes at least one of the group consisting of: whole blood, blood components, a peripheral blood cell collection, a bone marrow blood cell collection, and blood components removed from an umbilical cord.

39. The method of claim 33 wherein the liquid includes plasma.

40. The method of claim 33, wherein the ligands include at least one of the group consisting of: a protein, an antibody, a chemical composition, and mixtures thereof.

41. The method of claim 33, wherein the ligands include at least one antibody selected from the group consisting of: anti-CD2, anti-CD3, anti-CD4, anti-CD8, anti-CD9, anti-CD10, anti-CD14, anti-CD15, anti-CD19, anti-CD20, anti-CD34, anti-CD38, anti-CMRF-44, anti-CD45, anti-CD56, anti-CD93, anti-glycophorin, anti-cytokertin, anti-EPCAM, and combinations thereof.

42. The method of claim 33, wherein the ligands include at least one protein selected from the group consisting of: albumin and immunoglobulin.

43. The method of claim 33, wherein the ligands include at least one of the group consisting of: poloxamers and poly-lysine.

44. The method of claim 33, wherein an exterior surface of the first particles includes at least one of the group consisting of a surface modifying agent and poloxamer.

45. The method of claim 44, wherein the exterior surface of the first particles includes a surface modifying agent coomprising a polylactone-polysiloxane-polylactone triblock copolymer.

46. The method of claim 33, wherein the first particles are rigid, generally spherical beads.

47. The method of claim 33, wherein the second particles include at least one of the group consisting of: antigen-specific white blood cells, CD2+ cells, CD3+ cells, CD4+ cells, CD8+ cells, CD9+ cells, CD10+ cells, CD14+ cells, CD15+ cells, CD19+ cells, CD20+ cells, CD34+ cells, CD38+ cells, CMRF-44+ cells, CD45+ cells, CD56+ cells, CD83+ cells, glycophorin+ cells, cytokeratin+ cells, EPCAM+ cells, and combinations thereof.

48. The method of claim 33, wherein the third particles include at least one of the group consisting of: red blood cells, antigen-specific white blood cells, platelets, proteins, drugs, cytokines, and combinations thereof.

49. The method of claim 33, wherein the second and third particles include different types of antigen-specific white blood cells.

50. The method of claim 33, wherein the liquid carries antigen-specific white blood cells, the saturated fluidized bed of particles permitting at least some of the antigen-specific white blood cells to flow from the fluid chamber.

51. The method of claim 33, further comprising
passing into the fluid chamber a diluting liquid, the diluting liquid having a density less than that of the first, second, and third particles so that the diluting liquid reduces an overall density of substances in the fluid chamber and thereby limits Coriolis jetting of at least one of the liquid carrying the particles and the diluting liquid in the fluid chamber; and
allowing the diluting liquid to flow from the fluid chamber.

52. The method of claim 51, further comprising mixing the liquid carrying particles and the diluting liquid so that at least portions of the passing and flowing are performed simultaneously.

53. The method of claim 33, further comprising flowing the liquid and third particles from the fluid chamber into a separation vessel, separating the third particles from the liquid in the separation vessel, and collecting at least the third particles in a container.

54. The method of claim 33, further comprising adding an adhesion-reducing agent to the liquid carrying particles.

55. The method of claim 33, wherein the first particles include a dye, and wherein the method further comprises monitoring substances flowing from an outlet of the fluid chamber to detect the dye.

56. The method of claim 33, further comprising monitoring substances flowing from an outlet of the fluid chamber to detect first particles flowing from the outlet, and removing the first particles from the substances.

* * * * *